United States Patent
Roggenbuck

(10) Patent No.: US 11,340,235 B2
(45) Date of Patent: May 24, 2022

(54) GP2 ISOFORMS AND THEIR USE IN AUTOANTIBODY CAPTURE

(71) Applicant: GA GENERIC ASSAYS GMBH, Dahlewitz (DE)

(72) Inventor: Dirk Roggenbuck, Strausberg (DE)

(73) Assignee: GA GENERIC ASSAYS GMBH, Dahlewitz (DE)

( * ) Notice: Subject to any disclaimer, the term of this patent is extended or adjusted under 35 U.S.C. 154(b) by 155 days.

(21) Appl. No.: 16/707,016

(22) Filed: Dec. 9, 2019

(65) Prior Publication Data

US 2020/0209258 A1 Jul. 2, 2020

Related U.S. Application Data

(63) Continuation-in-part of application No. 14/634,740, filed on Feb. 28, 2015, now abandoned.

(30) Foreign Application Priority Data

Feb. 28, 2014 (EP) ..................................... 14157199

(51) Int. Cl.
*G01N 33/68* (2006.01)
(52) U.S. Cl.
CPC ..... *G01N 33/6854* (2013.01); *G01N 2333/47* (2013.01); *G01N 2800/24* (2013.01)
(58) Field of Classification Search
CPC ............. G01N 33/6854; G01N 33/564; G01N 2333/47; G01N 2800/06; G01N 2800/24
See application file for complete search history.

(56) References Cited

U.S. PATENT DOCUMENTS

| | | | |
|---|---|---|---|
| 4,292,403 A | 9/1981 | Duermeyer | |
| 7,608,414 B2 | 10/2009 | Dotan et al. | |
| 8,058,019 B2 | 11/2011 | Roggenbuck | |
| 9,617,873 B2 | 4/2017 | Eshak et al. | |
| 2010/0184662 A1* | 7/2010 | Roggenbuck | C07K 14/4733 514/19.3 |
| 2011/0130546 A1 | 6/2011 | Karrer et al. | |
| 2014/0147875 A1* | 5/2014 | Everson | G01N 33/92 435/21 |
| 2015/0247850 A1* | 9/2015 | Roggenbuck | G16B 40/00 435/7.92 |

FOREIGN PATENT DOCUMENTS

WO 2008089756 A2 7/2008

OTHER PUBLICATIONS

Davies et al., Long-term Treatment of Primary Sclerosing Cholangitis in Children With Oral Vancomycin: An Immunomodulating Antibiotic, Journal of Pediatric Gastroenterology and Nutrition: Jul. 2008—vol. 47—Issue 1—p. 61-67. (Year: 2008).*
Bogdanos et al. / Pancreatic-specific autoantibodies to glycoprotein 2 mirror disease location and behaviour in younger patients with Crohn's disease / BMC Gastroenterology 2012, 12:102http://www.biomedcentral.com/1471-230x/12/102.
Branka et al. / Autoantibodies to GP2, the major zymogen granule membrane glycoprotein, in patients with gluten-sensitive enteropathy: A possible serological trap / Clinica Chimica Acta 413 (2012) 822-823www.elsevier.com/locate/clinchim.
D. Roggenbruck et al. / Autoantibodies to GP2, the major zymogen granule membrane glycoprotein, are new markers in Crohn's disease / Clinica Chimica Acta 412 (2011) 718-724, www.elsevier.com/locate/clinchim.
D. Roggenbruck et al. / Crohn's disease specific pancreatic antibodies: clinical and pathophysiological challenges /DE Gruyter DOI 10.1515 / cclm-2013-0801—Clin Chem Lab Med 2014; 52 (4): 483-494.
Somma et al. / The Novel Crohn's Disease Marker Anti-GP2 Antibody is Associated with Ileocolonic Location of Disease / Hindawi Publishing Corporation / Gastroenterology Research and Practice vol. 2013, Article ID 683824, 7 pageshttp://dx.doi.org/10.1155/2013/6824.
Vallorani et al. / Anti glycoprotein-2 antibody in pediatric inflammatory bowel disease and celiac disease: prevalence, diagnostic value and variation at follow-up / 2014 /http://ecco-jcc.oxfordjournals.org/content/eccojc/8/Supplement_1/S179.2.full.pdf.

* cited by examiner

*Primary Examiner* — Shafiqul Haq
(74) *Attorney, Agent, or Firm* — Agris & Von Natzmer, LLP; Joyce Von Natzmer

(57) ABSTRACT

The invention relates to a method for binding or capturing autoantibodies directed to various Glycoprotein 2 (GP2) isoforms. In particular the invention provides an in vitro method for the diagnosis of an autoimmune disorder by the detection of autoantibodies that bind one or more isoforms of GP2. The invention is characterized by the provision of multiple isoforms of GP2 as autoantibody targets and encompasses the practical utilization of the finding that the isoform specificity of anti-GP2 autoantibodies enables determination of particular autoimmune diseases. The invention also provides a system and kit developed for carrying out the claimed method. The present invention is useful for determining whether a sample from an individual comprises autoantibodies associated with an autoimmune disease, and for differentiating between multiple autoimmune diseases that exhibit similar symptoms, such as Celiac disease (CeD), Crohn's disease (CD), primary sclerosing cholangitis (PSC), and/or ulcerative colitis (UC).

7 Claims, 9 Drawing Sheets

Specification includes a Sequence Listing.

A

B

A

B

GP2 ISOFORMS AND THEIR USE IN AUTOANTIBODY CAPTURE

CROSS REFERENCE TO RELATED APPLICATION

This application is a continuation-in-part of patent application Ser. No. 14/634,740, filed Feb. 28, 2015, incorporated herein by reference in its entirety, which claims priority to European application no. 14157199.2, filed on Feb. 28, 2014.

INCORPORATION OF SEQUENCE LISTING

This application contains a sequence listing submitted via the USPTO's EFS system and is incorporated herein by reference in its entirety. The sequence listing text file is named "7014-1840-Sequence-Listing", is 24 kilobytes (measured in MS-WINDOWS) and is dated Feb. 26, 2015.

FIELD OF THE INVENTION

The invention relates to a method for binding or capturing autoantibodies directed to various Glycoprotein 2 (GP2) isoforms. In particular the invention provides an in vitro method for the diagnosis of an autoimmune disorder by the detection of autoantibodies that bind one or more isoforms of GP2. The invention is characterized by the provision of multiple isoforms of GP2 as autoantibody targets and encompasses the practical utilization of the finding that the isoform specificity of anti-GP2 autoantibodies enables determination of particular autoimmune diseases. The invention also provides a kit and system developed for carrying out the claimed method. The present invention is useful for determining whether a sample from an individual comprises autoantibodies associated with an autoimmune disease, and for differentiating between multiple autoimmune diseases that exhibit similar symptoms, such as Celiac disease (CeD), Crohn's disease (CD), ulcerative colitis (UC) and/or primary sclerosing cholangitis (PSC).

BACKGROUND OF THE INVENTION

GP2 is a membrane glycoprotein of the acinar cells of the pancreas (Ronzio et al., 1978). GP2 has been detected in the brush-border cells of the intestine and as a component of lysosomes or as free, non-membrane-bound peptide in pancreatic juice. Making up 30 to 45% of the overall membrane protein, it represents the main component of the zymogen granule membrane. Together with other secretory pancreatic proteins of the zymogenic granules, such as syncollin, lectin ZG16p, synaptobrevin 2 and other sulfate matrix proteoglycans, GP2 is a component of lipid rafts of the granular membrane, and syncollin interacts with GP2. These complexes, also including other proteins such as ZG46p, form the submembranous matrix.

Glycoprotein 2 (GP2) has been identified as the main autoantigenic target of Crohn's disease (CD)-specific pancreatic antibodies (PAB) (Roggenbuck et al., 2009; Komorowski et al., 2012). Apart from its previously assumed restricted location in the pancreas, recent data have demonstrated that GP2 is also a constituent of microfold (M) cells of the follicle-associated epithelium, which appears to have an antimicrobial effect, like its renal homolog uromodulin (Tamm-Horsfall protein) (Hase et al., 2009; Terahara 2008). Additionally, emerging evidence indicates that GP2 is over-expressed at the site of intestinal inflammation in patients with CD, and that this molecule modulates innate and adaptive immune responses (Roggenbuck et al., 2009; Werner et al., 2012; Holz! et al., 2011)

Both CD and celiac disease (CeD) demonstrate inflammation of the intestine. However, the localization of the intestinal destruction and the pathophysiological mechanisms responsible for the induction of these diseases are quite distinct (Baumgart et al., 2007; Sollid, 2002). Nevertheless, the inflammatory processes seen in CD and CeD are believed to be exacerbated by or lead to an impairment of the intestinal barrier (Tibble et al., 2001; de KS et al., 2011). Growing evidence has been collected to demonstrate that both clinical entities involve the loss of humoral tolerance to self and microbiota antigens (Bossuyt, 2006; Bonifacio et al., 1995; Baekkeskov et al., 2000; Conrad et al., 2002). It has been shown in the art that loss of tolerance to GP2 is a characteristic feature of intestinal destruction in patients with CD (Bogdanos et al., 2012; Rieder et al., 2013; Roggenbuck et al., 2013).

Primary sclerosing cholangitis (PSC), a chronic immune-mediated, life threatening, genetically predisposed, cholestatic liver illness, is associated with the co-occurrence of inflammatory bowel disease (IBD) and in particular with the phenotype thereof. The prevalence of PSC is estimated at up to 16.2 per 100,000 individuals and still rising.

Loss of tolerance to GP2 has been reported in up to 30% of CD patients and to approximately 8-10% of patients with ulcerative colitis (UC), the other major inflammatory bowel disease (IBD) (Roggenbuck et al., Clin Chim Acta, 2011; Bogdanos et al., 2011; Op De et al., 2010). The clinical significance of these autoantibodies has been assessed and sero-positivity for anti-GP2 antibodies appears to identify CD patients with ileocolonic location, stenosing behaviour, and early disease onset (Bogdanos et al., 2012; Rieder et al., 2013; Pavlidis et al., 2012; Somma et al., 2013; Roggenbuck et al., Clin Chem Lab Med, 2013).

CD-related pathogenic autoantibodies (PAB) have been detected in patients with CeD, a chronic small intestinal immune-mediated enteropathy precipitated by exposure to dietary gluten in genetically predisposed individuals (Bonaci-Nikolic et al., 2012; Ludvigsson et al., 2012). Exposure to gluten in these patients triggers inflammatory processes leading to a variable degree of intestinal damage which is reversible with the initiation of gluten-free diet (GFD). The destructive mucosal changes detected in duodenal and jejunal biopsies lead to villous atrophy with hyperplasia of the crypts, a raised intraepithelial lymphocyte count, and an impairment of the intestinal barrier, a clinical complication also seen in patients with IBD (Soderholm et al., 1999; Bjarnason, 1994). In contrast to the mucosal inflammatory changes in CeD, the transmural inflammation in CD covers all layers of the bowel wall and adventitia and can occur throughout the intestinal tract (Baumgart et al., 2007). Severe tissue lesions such as fissures, abscesses, strictures, and fistulas can develop in the course of CD.

The immunopathogenesis of inflammatory bowel disease (IBD) as well as that of CeD are poorly understood (Rieder et al., 2011; Bardella et al., 2009). Antigen-driven mechanisms of immunological breakdown operate in both conditions, but it is still unclear whether the loss of tolerance to GP2 can also be seen in a sub-group of patients with CeD. If this feature is present, it could further indicate that an anti-GP2 response is initiated due to the damage of the intestinal barrier and the leaky gut (Fasano, 2012).

Two variants of GP2 have been described in 2000, which are produced in the humans due to alternative splicing (Fukuoka, 2000). In addition to the large form of GP2, containing 527 amino acids and termed alpha, a shorter beta form exists which comprises only 380 amino acids. The beta from seems to be dominantly expressed in human pancreatic tissue.

Currently, four isoforms of GP2 have been described (see tables 1 to 3 of the detailed description of the invention).

Although, according to a number of authors, the level of GP2 and the severity of IBD correlate, the physiological context is unknown. Furthermore, the physiological function of the four known isoforms of GP2 is still unclear.

Peptides having sequences highly similar to the large α-GP2 isoform are said to be responsible for pancreatic tumor formation. Antibodies to GP2 as analyte and marker are intended for use in diagnosing pancreatic cancer and the peptide and its nucleic acid sequence for use in immune therapy of cancerous diseases of the pancreas (WO 01/94409; US 2002/082,207). Antibodies to the small p-GP2 isoform find use as markers of pancreatitis (WO 96/17873; U.S. Pat. No. 5,663,315). An increase in p-GP2 concentration is said to be indicative of the disease.

Celiac disease (or known as coeliac disease or celiac sprue, "CeD") is an autoimmune disorder of the small intestine that occurs in people of all ages from infancy onward. Symptoms include pain and discomfort in the digestive tract, chronic constipation and diarrhea, anemia and fatigue, but these may be absent, and symptoms in other organ systems have been described.

Diagnosis of CeD can be carried out via multiple approaches, although none are considered entirely reliable. Serological blood tests are the first-line investigation required to make a diagnosis of CeD. Antiendomysial antibodies of the immunoglobulin A (IgA) type can detect CeD. Serology for anti-tTG antibodies may also be applied, whereby current anti-tTG assays rely on a human recombinant protein as an antigen.

CD and UC represent the two most important IBD. They are characterized by chronic, relapsing tissue-destroying inflammatory processes in the digestive system. To date, etiology and pathogenesis of CD as well as UC are unclear. While inflammation in UC predominantly appears in the mucosa and submucosa of colon and rectum, CD is characterized by wall-penetrating, granulomatous inflammatory processes of the entire gastrointestinal tract.

Highly complex and comparatively cost-intensive histological investigations of mucosa biopsies constitute common means in IBD (CD/UC) diagnostics. To this end, biopsies are collected especially from macroscopically conspicuous as well as inconspicuous areas. To efficiently utilize the potential of histopathological differential diagnostics it is, however, necessary to collect biopsies from at least five different anatomic segments of the entire colon, including the rectum, from the terminal ileum and upper gastrointestinal tract. Such analyses are time intensive and invasive, providing significant discomfort to the patient.

Straightforward diagnostic approaches for diagnosis of CeD, CD, PSC and UC remain elusive. Although some immunological assays have been developed, additional histological or biopsy-based analyses are often required. Autoantibodies against cytoskeletal proteins have been described in CD patients confirmed by means of biopsy. Autoantibodies against cytokeratin 18, actin, vimentin, desmin and tropomyosin have been found among others. Although cytokeratin 18 autoantibodies have been found to correlate with the activity of the disease, they failed to gain acceptance in IBD routine diagnostics, probably as a result of their low specificity. Explicit reference has been made to the necessary—still to be found—identification of the pancreatic autoantigen(s) in order to clarify the status of autoimmune processes in the pathogenesis of CD and support discrimination of unclear IBD cases by appropriate laboratory diagnostics.

GP2 has been identified previously as a biomarker for pancreatitis and antibodies directed against GP2 have been developed for interrogating GP2 levels in patients with IBD (WO 96/17873; U.S. Pat. No. 5,663,315). Autoantibody-based diagnostics involving GP2 as an autoantigen have been described previously (WO 2008/089756 A2; U.S. Pat. No. 8,058,019). Anti-GP2 autoantibodies have been described in some patients with CeD (Bonaci-Nikolic Branka et al, Clinica Chimica Acta 413 (2012) 822-823). However, no isoform-specificity of the autoantibodies has been disclosed previously and differentiation between CD and CeD has been neither disclosed, nor is possible, based on the methods disclosed in the art.

Despite the various assays available for CD, UC or CeD diagnosis, there is still significant uncertainty regarding which approach is ideal.

Furthermore, due to the overlapping symptoms between each of these diseases, most molecular and histological assays are still considered sub-optimal, if not entirely unable to distinguish between separate autoimmune disorders of the gastrointestinal tract. For example, WO 2011/130546 A1 describes a method for distinguishing CD from other autoimmune conditions based on a composite microbial antibody score, which requires a complex analysis in order to enable identification of the conditions. Effective and straightforward molecular diagnostic means are required that effectively provide differentiation between each of the conditions via immunological assays.

All references referred to herein, including patents and patent applications, are incorporated herein by reference in their entirety. Non-patent literature referenced herein are also listed the appended list entitled "Literature."

BRIEF DESCRIPTION OF THE FIGURES

Without intending to be limiting, the invention will be explained in more detail with reference to the figures.

References in the figures to CrD refer to CD.

Figure 9:
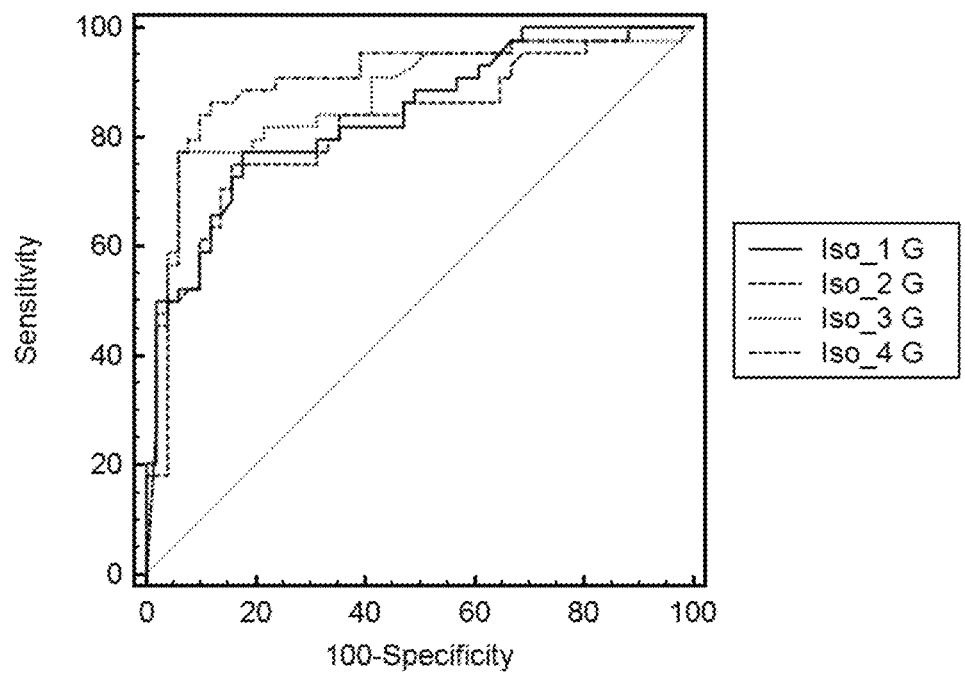
Figure 9:
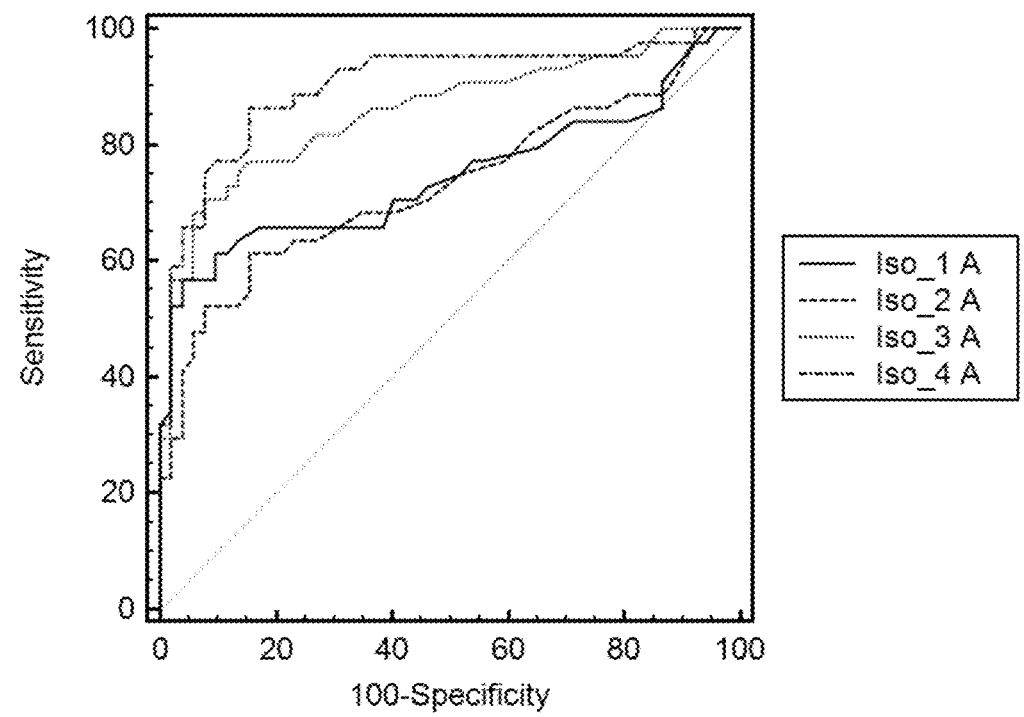

FIG. 9: Receiver operating characteristics curve analysis of IgG (A) and IgA (B) to 4 different GP2 isoforms in 44 patients with CD, 30 patients with UC and 21 blood donors.

Figure 10:
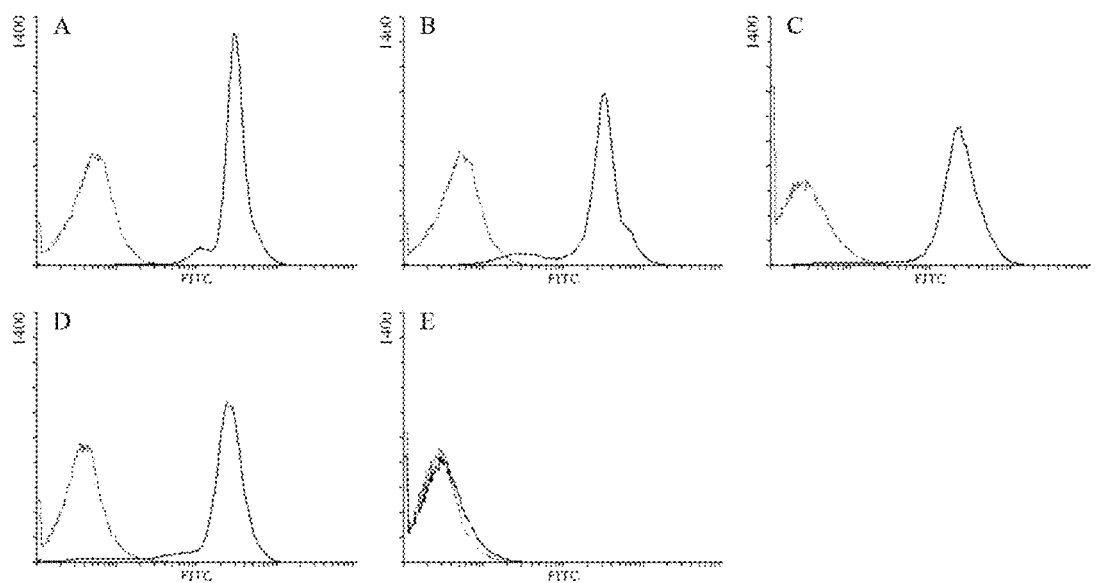

FIG. 10: Detection of the membrane expression of GP2 isoforms in HEp-2 cells by flow cytometry: GP2 expressed in HEp-2 cells was stained with polyclonal antibodies raised against full length human GP2 followed by FITC-conjugated anti-rabbit IgG: A) HEp-2 cells expressing human GP2 isoform 1; B) GP2 isoform 2; C) GP2 isoform 3; D) GP2 isoform 4; E) HEp-2 cells transduced with an empty vector; black solid lines: primary and secondary antibody staining; black dotted lines: secondary antibody staining only.

Figure 11:
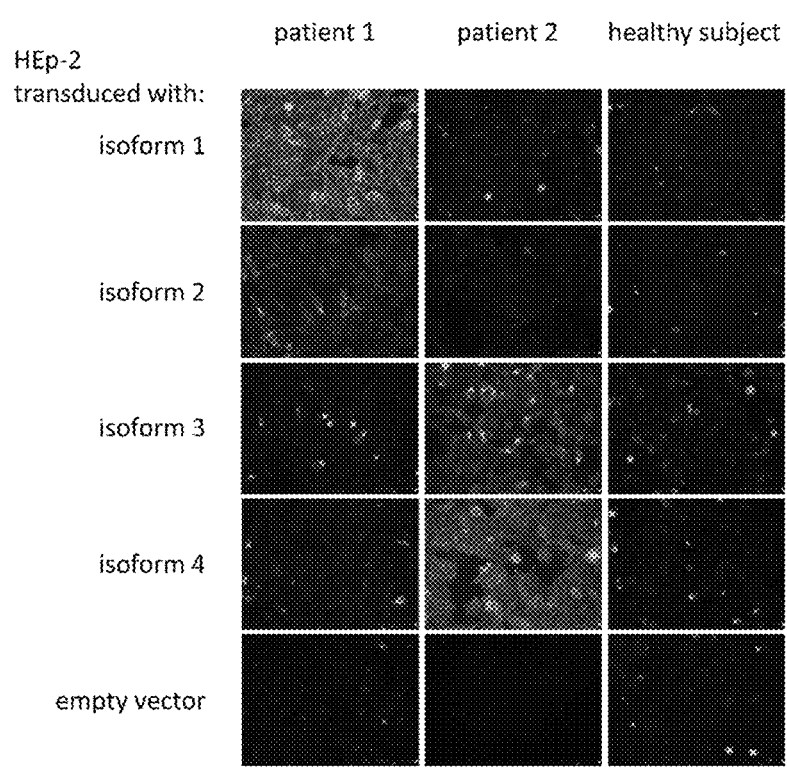

FIG. 11: Indirect immunofluorescence assay for the detection of IgA to GP2 isoforms: Exemplarily, two patient sera and one serum of a healthy subject as control were run on HEp-2 cells transduced with GP2 isoforms 1 (GP21) to 4 (GP24) with glycosylphosphatidylinositol anchor and an empty vector, respectively. Patient 1 demonstrated a strong specific binding to membrane-bound GP21 and a weak one to GP22, whereas patient 2 showed the typical binding pattern for a strong positive binding to GP24 and a relatively weak one for GP23. The healthy subject did not reveal a positive membrane-reactive pattern on the respective transduced HEp-2 cells.

SUMMARY OF THE INVENTION

There remains a need for a system and method for diagnosing CeD, CD and/or UC that do not exhibit the disadvantages of the prior art. There remains also a need for a system and method for differentiating between CeD, CD and/or UC, for example in patients with similar symptoms of disease.

There remains a need for method for diagnosing PSC, including severity, prognosis and/or cholangiocarcinoma in PSC.

The present invention address this and/or other needs in the art.

The invention therefore relates to an in vitro method for the diagnosis of an autoimmune disorder by detection of autoantibodies from a sample that bind to one or more isoforms of Glycoprotein 2 (GP2), comprising providing a sample of a subject exhibiting symptoms and/or suspected of having said disorder,
providing two or more isoforms of Glycoprotein 2 (GP2), wherein at least one of isoforms 1 and/or 2 (such as SEQ ID NO 1 and/or 2) and at least one of isoforms 3 and/or 4 (such as SEQ ID NO 3 and/or 4) are provided,
contacting said sample with said GP2 isoforms, and
detecting autoantibodies from said sample that bind to one or more isoforms.

The invention relates to the surprising and unexpected finding that different isoforms of the GP2 protein are targets for autoantibodies that are associated with different autoimmune diseases.

The various GP2 isoforms, preferably according to those sequences described herein, may therefore be used in the diagnosis and/or differentiation of autoimmune disease, in particular autoimmune disorders associated with autoantibodies that bind components of the digestive or intestinal (gastrointestinal) tract of said subject, in particular Celiac disease (CeD), or inflammatory bowel disease (IBD), such as Ulcerative colitis (UC) and/or Crohn's disease (CD).

According to the present invention the components of the gastrointestinal tract, to which autoantibodies may bind, include, but are not limited to, the mucosa of the small intestine or other small-bowel tissue, the villous extracellular matrix, intestinal epithelial cells, in particular villous epithelial cells, the endomysium or other tissues or cells of the stomach, small intestine, and colon, in particular the cells lining of the stomach, small intestine, and colon.

It was at the time of the invention entirely unknown that the various isoforms of GP2 could be used as an epitope or target to distinguish between the presence or absence of different autoimmune diseases, preferably those characterized by autoantibodies that bind components of the gastrointestinal tract of a subject.

The method thereby allows differentiation between such diseases on the basis of their distinct autoantibody profiles, which target only a subset of the GP2 isoforms provided herein. The use of multiple GP2 isoforms thereby represents a novel and inventive concept in light of the prior art with respect to the diagnosis of autoimmune diseases using GP2 as a target.

The use of multiple GP2 isoforms as autoantibody targets in diagnostics is common to preferred embodiments of the invention, thereby representing a unifying concept that is novel and unexpected in light of the cited art.

In a preferred embodiment of the method the isoforms are selected from proteins comprising or consisting of:
amino acid sequences of isoforms 1, 2, 3 and/or 4 of SEQ ID NO 1, 2, 3 and/or 4, respectively, or
amino acid sequences of more than 80%, more than 85%, more than 90% or more preferably more than 95% sequence identity to SEQ ID NO 1, 2, 3 and/or 4.

The isoforms of GP2 also relate to those of substantially the same amino acid sequence as those explicitly listed. This refers to one or more amino acid sequence that is similar, but not identical to, the amino acid sequence provided explicitly herein.

Variation in length of the amino acid sequences and encoding nucleic acids as described herein is also encompassed by the present invention. A skilled person is capable of providing artificial amino acid sequence variants that are longer or shorter than the specific sequences of SEQ ID NO 1 to 4, which will still exhibit sufficient similarity to the natural forms in order to provide the diagnostic outcomes described herein. For example, shorter variants of the longer isoforms (SEQ ID NO 1 or 2) comprising 10, 20, 30, 40 or 50 amino acids less than the full length form are also part of the present invention to enable effective diagnostic outcomes, as described herein. For example, longer variants of the shorter isoforms (SEQ ID NO 3 or 4) comprising 10, 20, 30, 40 or 50 amino acids of GP2 sequence more than the natural length form are also part of the present invention to enable also enable effective diagnostic outcomes, as described herein.

In one aspect of the invention, the method relates to a method for the diagnosis of Celiac disease (CeD), wherein the presence of IgG and/or IgA autoantibodies from a sample of said subject that bind to isoforms 1 and/or 2 of GP2 (SEQ ID NO 1 and/or 2) indicates the presence of CeD. This effect is preferably specific to the isoforms 1 and 2. The provision of at least two isoforms, at least one of 3 and/or 4 and at least one of 1 and/or 2, enables more sound CeD diagnosis than was previously possible. This embodiment is therefore also characterized by the unexpected findings related to isoform-specificity of the anti-GP2 autoantibodies.

The invention therefore relates to the method as described herein for the diagnosis of Celiac disease (CeD), wherein an increased or larger amount of IgG and/or IgA autoantibodies that bind isoforms 1 and/or 2 of GP2 (SEQ ID NO 1 and/or 2) compared to IgG and/or IgA autoantibodies that bind isoforms 3 and/or 4 (SEQ ID NO 3 and/or 4) in a sample of a subject indicates the presence of CeD in said subject.

In a further embodiment the method as described herein comprises:
measuring an amount of IgG and/or IgA autoantibodies that bind isoforms 1 and/or 2 of GP2 (SEQ ID NO 1 and/or 2) and an amount of IgG and/or IgA autoantibodies that bind isoforms 3 and/or 4 (SEQ ID NO 3 and/or 4) in the sample;
comparing the amount of IgG and/or IgA autoantibodies that bind isoforms 1 and/or 2 of GP2 (SEQ ID NO 1 and/or 2) with the amount of IgG and/or IgA autoantibodies that bind isoforms 3 and/or 4 (SEQ ID NO 3 and/or 4), wherein when the amount of IgG and/or IgA autoantibodies that bind isoforms 1 and/or 2 of GP2 (SEQ ID NO 1 and/or 2) is higher than the amount of IgG and/or IgA autoantibodies that bind isoforms 3 and/or 4 (SEQ ID NO 3 and/or 4) the subject is diagnosed with Celiac disease.

In one aspect of the invention, the method relates to a method for the diagnosis of Crohn's disease (CD), wherein the presence of IgG and/or IgA autoantibodies from a sample of said subject that bind to isoforms 1, 2, 3 and/or 4 of GP2 (SEQ ID NO 1, 2, 3 and/or 4), preferably isoforms 2, 3 and/or 4 (SEQ ID NO 2, 3 and/or 4), more preferably isoforms 3 and/or 4 (SEQ ID NO 3 and/or 4), indicates the presence of CD.

It has been shown for the first time that autoantibodies in patients with CD that bind GP2 bind the comparatively shorter forms of GP2, namely isoforms 3 and/or 4. This embodiment is therefore characterized by the unexpected findings related to isoform-specificity of the anti-GP2 autoantibodies.

The invention therefore relates to the method as described herein for the diagnosis of Crohn's disease (CD), wherein an increased or larger amount of IgG and/or IgA autoantibodies that bind isoforms 3 and/or 4 of GP2 (SEQ ID NO 3 and/or 4) compared to IgG and/or IgA autoantibodies that bind isoforms 1 and/or 2 (SEQ ID NO 1 and/or 2) in a sample of said subject indicates the presence of CD in said subject.

In a further embodiment the method as described herein comprises:
measuring an amount of IgG and/or IgA autoantibodies that bind isoforms 1 and/or 2 of GP2 (SEQ ID NO 1 and/or 2) and an amount of IgG and/or IgA autoantibodies that bind isoforms 3 and/or 4 (SEQ ID NO 3 and/or 4) in the sample;
comparing the amount of IgG and/or IgA autoantibodies that bind isoforms 1 and/or 2 of GP2 (SEQ ID NO 1 and/or 2) with the amount of IgG and/or IgA autoantibodies that bind isoforms 3 and/or 4 (SEQ ID NO 3 and/or 4), wherein when the amount of IgG and/or IgA autoantibodies that bind isoforms 3 and/or 4 of GP2 is higher than the amount of IgG and/or IgA autoantibodies that bind isoforms 1 and/or 2 the subject is diagnosed with Crohn's disease.

The method also relates to a method as essentially described herein, whereby said method may be described as an in vitro method for the detection of autoantibodies from a sample that bind to one or more isoforms of Glycoprotein 2 (GP2), comprising one or more of the features described herein.

The provision of the sample to be analysed may relate to either obtaining a sample from a patient, or providing a pre-prepared sample already having been obtained, preferably from a patient exhibiting symptoms and/or suspecting of having an autoimmune disorder, preferably an autoimmune disorder associated with autoantibodies that bind components of the digestive or intestinal tract of said subject.

Examples of the symptoms of said disorders are provided herein and are not intended to limit the scope of the invention. Such symptoms are well-known to skilled practitioners in the field.

Any reference to the provision of multiple isoforms comprises the provision of more than one isoform for analysis. The multiple isoforms may be used in the method as described either simultaneously, one after the other, also at different time points during various diagnostic procedures, for example minutes, hours, weeks or months apart. In some embodiments of the invention one isoform alone may be used, for example in follow up analyses for confirmation. The use of multiple isoforms preferably relates to the simultaneous use of multiple isoforms, for example when the isoforms are attached to a single solid phase for analysis with a single sample, or on separate solid phases for analysis of a single sample at the same time (in other words under the same conditions).

The sample of the present invention relates preferably to a sample obtained from a patient, such as a bodily fluid, preferably a blood, plasma or serum sample, but may also relate to stool sample. Tissue samples may also be used in the method of the invention. Any particular processing of the sample is not intended to be limiting to the scope of the invention, essentially any given sample obtained from the patient may be used, with or without additional processing steps before administration in the method described herein.

The contacting of a sample to the GP2 isoforms may take place in any given setting. In one embodiment, a solid phase, to which the isoforms are attached, is used. The sample is preferably provided as a liquid sample and is brought into contact with the GP2 isoforms, thereby allowing the autoantibodies of the sample to interact with the GP2 isoforms under conditions that allow binding of said antibodies to the GP2 epitope. Such conditions are known to a skilled person and may represent biological conditions, in which the relevant proteins are capable of forming their native or nearnative structures, in order to allow the binding properties of the antibodies to enable interaction with said isoforms.

The contacting and detection steps may in further embodiments be carried out as follows: allowing the antibody to bind the one or more GP2 isoforms, thereby forming a complex (GP2-autoantibody complex), contacting the complex with a label, such as a labeled indicator antibody, preferably an antibody that binds human immunoglobulin, to form a labeled complex; and detecting the presence or absence of the labeled complex, and preferably associating the presence of the detected antibodies in the sample with the autoimmune disease.

The detection of bound antibodies may be carried out in any given suitable manner, including but not limited to the use of a spectrophotometer to detect color from a chromogenic substrate, a radiation counter to detect radiation such as a gamma counter for detection of 125I, or a fluorometer to detect fluorescence in the presence of light of a certain wavelength.

Washing of the bound antibodies may be carried out as is commonly known in the art, for example as is carried out in a standard immunoassay, such as an ELISA assay. Additional detection means are described herein.

It was at the time of the invention entirely unknown that the various isoforms of GP2 could be used as an epitope or target to distinguish between the presence or absence of different autoimmune diseases, preferably those characterized by autoantibodies that bind components of the gastrointestinal tract of a subject. The method allows differentiation between such diseases on the basis of their distinct autoantibody profiles, which target only a subset of the GP2 isoforms provided herein. The use of multiple GP2 isoforms thereby represents a novel and inventive concept in light of the prior art with respect to the diagnosis of autoimmune diseases using GP2 as a target.

The method thereby may allow the differentiation of autoimmune diseases, which may show very similar disease symptoms with respect to digestive problems, stomach cramps and pain, diarrhea, amongst others, via a simple and cost effective immunoassay, such as an ELISA, thereby avoiding more complicated diagnostic procedures such as endoscopies or biopsy analysis.

In one embodiment the method of the present invention is characterized in that said method provides differentiation of an autoimmune disorder, characterized by autoantibodies that bind components of the gastrointestinal tract of said subject, from one or more other autoimmune disorders also characterized by autoantibodies that bind components of the gastrointestinal tract of said subject.

In one embodiment the method of the present invention is characterized in that said disorder is associated with autoantibodies that bind one or more, but not all, isoforms 1 to 4 of GP2 according to SEQ ID NO 1 to 4. As demonstrated in the experimental examples herein, in some embodiments of the invention the autoantibody populations bind only a subset of the GP2 isoforms, in particular either the long or short forms of the GP2 protein, and not both. For example, the autoantibodies of celiac patients bind only isoforms 1 and 2.

The invention provides the surprising development over known methods in the field that anti-GP2 autoantibodies of CeD patients bind exclusively the isoforms 1 and/or 2 of GP2, whereby isoforms 3 and/or 4 are bound preferably by the autoantibody population of CD patients. The recognition of this fact enables the method as described herein with respect to differentiation between CD and UC, in particular due to the identification of autoantibodies that bind isoform 3 and/or 4, preferably 4, which indicates the presence of CD, and preferably the absence of CeD and/or UC.

The present invention therefore also relates to a method as described herein for the diagnosis of diagnosis of Celiac disease (CeD) and differentiation from Crohn's disease (CD), wherein a larger amount of IgG and/or IgA autoantibodies that bind isoforms 1 and/or 2 of GP2 (SEQ ID NO 1 and/or 2) compared to IgG and/or IgA autoantibodies that bind isoforms 3 and/or 4 (SEQ ID NO 3 and/or 4) in a sample of said subject indicates the presence of CeD and the absence of CD in said subject.

The present invention further relates to a method as described herein for diagnosis of Crohn's disease (CD) and differentiation from Celiac disease (CeD) and/or Ulcerative colitis (UC).

The present invention further relates to a method as described herein for the diagnosis of Crohn's disease (CD), wherein a larger amount of IgG and/or IgA autoantibodies from a sample of said subject bind to isoforms 3 and/or 4 of GP2 (SEQ ID NO 3 and/or 4) than to isoforms 1 and/or 2 (SEQ ID NO 1 and/or 2) indicates the presence of CD.

The present invention therefore also relates to a method as described herein for the diagnosis of diagnosis of Crohn's disease (CD) and differentiation from Celiac disease (CeD) and/or Ulcerative colitis (UC), wherein a larger amount of IgG and/or IgA autoantibodies that bind isoforms 3 and/or 4 of GP2 (SEQ ID NO 3 and/or 4) compared to IgG and/or IgA autoantibodies that bind isoforms 1 and/or 2 (SEQ ID NO 1 and/or 2) in a sample of said subject indicates the presence of CD and the absence of CeD and/or UC in said subject.

The present invention further relates to a method as described herein for differentiation between Ulcerative colitis (UC) and Crohn's disease (CD), wherein a larger amount of IgG and/or IgA autoantibodies from a sample of said subject that bind to isoforms 3 and/or 4 of GP2 (SEQ ID NO 3 and/or 4) than to isoforms 1 and/or 2 (SEQ ID NO 1 and/or 2) indicates the presence of CD, and preferably the absence of CU.

The method of the present invention may in one or more embodiments comprise treatment of the autoimmune disease identified. Potential treatments are mentioned below.

The invention further provides a system and/or kit for the diagnosis of an autoimmune disorder by the detection of autoantibodies from a sample that bind to one or more isoforms of Glycoprotein 2 (GP2), comprising one or more isoforms of GP2, comprising two or more isoforms of GP2), wherein at least one of isoforms 1 and/or 2 (SEQ ID NO 1 and/or 2) and at least one of isoforms 3 and/or 4 (SEQ ID NO 3 and/or 4) are present.

The invention further provides a system and/or kit for the diagnosis of an autoimmune disorder by the detection of autoantibodies from a sample that bind to one or more isoforms of Glycoprotein 2 (GP2) according to the preceding claim, comprising:
  at least one amino acid sequence of isoforms 1 and/or 2 (SEQ ID NO 1 and/or 2) and at least one amino acid sequence of isoforms 3 and/or 4 (SEQ ID NO 3 and/or 4), or amino acid sequences of more than 80%, more than 85%, more than 90% or more preferably more than 95% sequence identity to isoforms 1, 2, 3 and/or 4 (SEQ ID NO 1, 2, 3 and/or 4), and/or
  at least one nucleic acid molecule encoding an isoforms 1 and/or 2 (SEQ ID NO 1 and/or 2) and at least one nucleic acid molecule encoding isoforms 3 and/or 4 (SEQ ID NO 3 and/or 4), such as those according to SEQ ID NO 5 to 8, or a nucleic acid molecule comprising a degenerate sequence thereof, or a complementary sequence thereof, or a sequence of more than 80%, more than 85%, more than 90% or more preferably more than 95% sequence identity to any one or more of SEQ ID NO 5 to 8.

The invention therefore also relates to the use of the nucleic acid molecules in the method, system or kit as described herein, wherein said nucleic acid molecules may comprise a sequence encoding isoforms 1, 2, 3 and/or 4 (SEQ ID NO 1, 2, 3 and/or 4), such as those according to SEQ ID NO 5 to 8, or a nucleic acid molecule comprising a degenerate sequence thereof, or a complementary sequence thereof, or a sequence of more than 80%, more than 85%, more than 90% or more preferably more than 95% sequence identity to any one or more of SEQ ID NO 5 to 8.

As described herein, the finding that different isoforms of GP2 are targets for autoantibodies that are associated with specific autoimmune diseases is a surprising and unexpected finding as such.

Therefore the combination of multiple isoforms of GP2 in a format appropriate for carrying out the present method is motivated only by the novel and surprising finding of the present invention. The combination of multiple GP2 isoforms as such is therefore to be considered an unexpected development of the art. There exists no suggestion in the relevant literature that the provision of a kit comprising multiple GP2 isoforms for carrying out the present method should have been developed.

In a preferred embodiment the system or kit of the present invention is characterized in that said kit comprises:

amino acid sequences of isoforms 1 and/or 2 (SEQ ID NO 1 and/or 2) and isoforms 3 and/or 4 (SEQ ID NO 3 and/or 4), and amino acid sequences of more than 80%, more than 85%, more than 90% or more preferably more than 95% sequence identity to isoforms 1 and/or 2 (SEQ ID NO 1 and/or 2) and isoforms 3 and/or 4 (SEQ ID NO 3 and/or 4), or nucleic acid molecule comprising a sequence encoding isoforms 1 and/or 2 (SEQ ID NO 1 and/or 2) and isoforms 3 and/or 4 (SEQ ID NO 3 and/or 4), such as those according to SEQ ID NO 5 to 8, and/or a nucleic acid molecule comprising a degenerate sequence thereof, and/or a complementary sequence thereof, and/or a sequence of more than 80%, more than 85%, more than 90% or more preferably more than 95% sequence identity to any one or more of SEQ ID NO 5 to 8.

In one embodiment the kit of the present invention is characterized in that said kit comprises a solid phase to which at least one amino acid sequence of isoforms 1 and/or 2 (SEQ ID NO 1 and/or 2) and at least one amino acid sequence of isoforms 3 and/or 4 (SEQ ID NO 3 and/or 4), or amino acid sequences of more than 80%, more than 85%, more than 90% or more preferably more than 95% sequence identity to isoforms 1 and/or 2 (SEQ ID NO 1 and/or 2) and isoforms 3 and/or 4 (SEQ ID NO 3 and/or 4), are immobilized.

In one embodiment the kit of the present invention comprises additionally:

one or more human anti-immunoglobulin antibodies, wherein said human anti-immunoglobulin antibodies bind autoantibodies of Ig-subtypes IgG, IgA and/or IgM, a label, either capable of binding said human anti-Immunoglobulin antibody, or linked to said anti-Immunoglobulin antibody, and means for detecting said label.

The embodiments described herein with reference to the kit of the present invention are intended to also relate to structural features of the components of the method as described herein. The features of the kit as described herein may therefore also be used to characterize the method, and vice versa.

The invention therefore also relates to the use of a kit as described herein for the diagnosis of an autoimmune disorder by the detection of autoantibodies from a sample that bind to at least one amino acid sequence of isoforms 1 and/or 2 (SEQ ID NO 1 and/or 2) and/or at least one amino acid sequence of isoforms 3 and/or 4 (SEQ ID NO 3 and/or 4).

The invention further relates to a system for the diagnosis of an autoimmune disorder by the detection of autoantibodies from a sample that bind to one or more isoforms of Glyco-protein 2 (GP2), comprising one or more isoforms of GP2, comprising two or more isoforms of GP2), wherein at least one of isoforms 1 and/or 2 and at least one of isoforms 3 and/or 4 are present.

In one embodiment the system comprises: a computer system, and optionally, e.g., as part of the computer system, one or more of the following: one or more data processing device, which may be networked, configured to perform executable instructions; one or more computer programs, the one or more computer programs comprising one or more software modules preferably executed by the data processing device to apply a model or algorithm for analyzing data, e.g. of bound autoantibodies. In one embodiment, two computer programs are provided, one for storing data received from the sample analyzer and one for comparing the data according to certain criteria, e.g., predetermined parameters, such as the relative amount of autoantibodies that bind isoforms 1 and/or 2 of GP2, and amounts of autoantibodies that bind isoforms 3 and/or 4 of GP2 may be compared to each other and the result may be processed to provide diagnostic data.

In one embodiment the system is configured to designate and may actually designate a treatment regimen for the individual.

In one embodiment the system is configured so that a patient from which said sample has been taken is identified as providing said sample and is optionally treated for the autoimmune disease.

Treatment for an autoimmune disease of the gastrointestinal tract may relate to any appropriate treatment known to a skilled medical practitioner. Medical treatment of IBD may be individualized to each patient. The choice of which drugs to use and by which route to administer them (oral, rectal, injection, infusion) depends on factors including the type, distribution, and severity of the patient's disease, as well as other historical and biochemical prognostic factors, and patient preferences. For example, mesalazine may be administered. Generally, depending on the level of severity, autoimmune IBD may require immuno-suppression to control the symptoms, such as prednisone, TNF inhibition, azathioprine (Imuran), methotrexate, or 6-mercaptopurine administration. Often, anti-inflammatory steroids are used to control disease flares. Crohn's disease and ulcerative colitis patients may receive TNF inhibitors. Severe cases may require surgery, such as bowel resection or a temporary or permanent colostomy or ileostomy. Surgery can cure ulcerative colitis if the large intestine is removed. A pouch can be created from the small intestine when required, this serves as the rectum and prevents the need for a permanent ileostomy.

In one embodiment the system is configured to analyze in a sample from a subject an amount of autoantibodies that bind two or more isoforms of Glycoprotein 2 (GP2), wherein the system categorizes the autoantibodies into groups, wherein the groups comprise group 1 autoantibodies that bind to isoforms 1 and/or 2 (SEQ ID NO 1 and/or 2) and group 2 autoantibodies that bind to isoforms 3 and/or 4 (SEQ ID NO 3 and/or 4), and the system attributes the sample to a disorder selected from such as Celiac disease (CeD), Crohn's disease (CD) and/or ulcerative colitis (UC), or to a heathy group based on the amount of group 1 or group 2 autoantibodies measured.

In one embodiment the system comprises:

optionally, two or more isoforms of GP2 comprising at least one of isoform 1 and/or 2 of GP2 and at least one of isoform 3 and/or 4 of GP2;

a sample analyzer configured to determine an amount of autoantibodies in the sample that bind to said two or more isoforms of Glycoprotein 2 (GP2), and a computer system configured to receive and/or analyze data obtained from the sample analyzer, and for correlating the amount of the autoantibodies with a diagnosis of Celiac disease (CeD), Crohn's disease (CD) and/or ulcerative colitis (UC).

The computer system may correlate the amount of the autoantibodies with a diagnosis of Celiac disease (CeD), Crohn's disease (CD) and/or ulcerative colitis (UC) according to:

parameter 1 (P1): amount of IgG and/or the IgA autoantibodies that bind isoforms 1 and/or 2 of GP2, and parameter 2 (P2): amount of IgG and/or the IgA autoantibodies that bind isoforms 3 and/or 4 of GP2, wherein the system specifies a presence or an absence of CeD, CD and/or UC according to following criteria:

P1>P2=CeD; or CeD and ≠CD, and

P1<P2=CD; or CD and ≠CD and/or ≠UC, wherein "=" denotes the presence of a subsequently named disease and "≠" denotes the absence of the subsequently named disease.

Sample analysers and computer systems that interact with such sample analysers are, e.g., described in US Patent Publication 20090265116.

DETAILED DESCRIPTION OF VARIOUS AND PREFERRED EMBODIMENTS OF THE INVENTION

TABLE 1

Terminology of GP2 isoforms

| Amino acids | | Pubmed # |
|---|---|---|
| 537 | Isoform 1 SEQ ID NO. 1 | NP_001007241.2 |
| 534 | Isoform 2 SEQ ID NO. 2 | NP_001493.2 |
| 390 | Isoform 3 SEQ ID NO. 3 | NP_001007242.2 |
| 387 | Isoform 4 SEQ ID NO. 4 | NP_001007243.2 |

TABLE 2

Amino Acid sequences of isoforms 1 to 4

| SEQ ID NO. | Amino Acid Sequence | Description |
|---|---|---|
| SEQ ID NO 1 | MPHLMERMVGSGLLWLALVSCILTQASAVQRGYGNPIEAS SYGLDLDCGAPGTPEAHVCFDPCQNYTLLDEPFRSTENSA GSQGCDKNMSGWYRFVGEGGVRMSETCVQVHRCQTDA PMWLNGTHPALGDGITNHTACAHWSGNCCFWKTEVLVKA CPGGYHVYRLEGTPWCNLRYCTVPRDPSTVEDKCEKACR PEEECLALNSTWGCFCRQDLNSSDVHSLQPQLDCGPREIK VKVDKCLLGGLGLGEEVIAYLRDPNCSSILQTEERNWVSVT SPVQASACRNILERNQTHAIYKNTLSLVNDFIIRDTILNINFQ CAYPLDMKVSLQAALQPIVSSLNVSVDGNGEFIVRMALFQD QNYTNPYEGDAVELSVESVLYVGAILEQGDTSRFNLVLRN CYATPTEDKADLVKYFIIRNSCSNQRDSTIHVEENGQSSES RFSVQMFMFAGHYDLVFLHCEIHLCDSLNEQCQPSCSRSQ VRSEVPAIDLARVLDLGPITRRGAQSPGVMNGTPSTAGFLV AWPMVLLTVLLAWLF | Transcript Variant: This variant (1) represents the longest transcript, although it occurs rarely. It encodes the longest protein (iso- form 1). |
| SEQ ID NO 2 | MPHLMERMVGSGLLWLALVSCILTQASAVQRGYGNPIEAS SYGLDLDCGAPGTPEAHVCFDPCQNYTLLDEPFRSTENSA GSQGCDKNMSGWYRFVGEGGVRMSETCVQVHRCQTDA PMWLNGTHPALGDGITNHTACAHWSGNCCFWKTEVLVKA CPGGYHVYRLEGTPWCNLRYCTDPSTVEDKCEKACRPEE ECLALNSTWGCFCRQDLNSSDVHSLQPQLDCGPREIKVKV DKCLLGGLGLGEEVIAYLRDPNCSSILQTEERNWVSVTSPV QASACRNILERNQTHAIYKNTLSLVNDFIIRDTILNINFQCAY PLDMKVSLQAALQPIVSSLNVSVDGNGEFIVRMALFQDQN YTNPYEGDAVELSVESVLYVGAILEQGDTSRFNLVLRNCYA TPTEDKADLVKYFIIRNSCSNQRDSTIHVEENGQSSESRFS VQMFMFAGHYDLVFLHCEIHLCDSLNEQCQPSCSRSQVRS EVPAIDLARVLDLGPITRRGAQSPGVMNGTPSTAGFLVAW PMVLLTVLLAWLF | Transcript Variant: This variant (2) lacks an al- ternate in-frame segment, compared to variant 1. The resulting protein (isoform 2) is shorter than isoform 1. Isoform 2 is also known as the alpha form. |
| SEQ ID NO 3 | MPHLMERMVGSGLLWLALVSCILTQASAVQRVPRDPSTVE DKCEKACRPEEECLALNSTWGCFCRQDLNSSDVHSLQPQ LDCGPREIKVKVDKCLLGGLGLGEEVIAYLRDPNCSSILQTE ERNWVSVTSPVQASACRNILERNQTHAIYKNTLSLVNDFIIR DTILNINFQCAYPLDMKVSLQAALQPIVSSLNVSVDGNGEFI VRMALFQDQNYTNPYEGDAVELSVESVLYVGAILEQGDTS RFNLVLRNCYATPTEDKADLVKYFIIRNSCSNQRDSTIHVEE NGQSSESRFSVQMFMFAGHYDLVFLHCEIHLCDSLNEQCQ | Transcript Variant: This variant (3) lacks an al- ternate in-frame segment, compared to variant 1. The resulting protein (isoform 3) has a shorter N-terminus when compared to iso- |

TABLE 2-continued

Amino Acid sequences of isoforms 1 to 4

| SEQ ID NO. | Amino Acid Sequence | Description |
| --- | --- | --- |
| | PSCSRSQVRSEVPAIDLARVLDLGPITRRGAQSPGVMNGT<br>PSTAGFLVAWPMVLLTVLLAWLF | form 1, although the 31 most N-term aas are maintained. |
| SEQ ID NO 4 | MPHLMERMVGSGLLWLALVSCILTQASAVQRDPSTVEDKC<br>EKACRPEEECLALNSTWGCFCRQDLNSSDVHSLQPQLDC<br>GPREIKVKVDKCLLGGLGLGEEVIAYLRDPNCSSILQTEER<br>NWVSVTSPVQASACRNILERNQTHAIYKNTLSLVNDFIIRDT<br>ILNINFQCAYPLDMKVSLQAALQPIVSSLNVSVDGNGEFIVR<br>MALFQDQNYTNPYEGDAVELSVESVLYVGAILEQGDTSRF<br>NLVLRNCYATPTEDKADLVKYFIIRNSCSNQRDSTIHVEEN<br>GQSSESRFSVQMFMPAGHYDLVFLHCEIHLCDSLNEQCQP<br>SCSRSQVRSEVPAIDLARVLDLGPITRRGAQSPGVMNGTP<br>STAGFLVAWPMVLLTVLLAWLF | Transcript Variant: This variant (4) lacks two alternate in-frame segments, compared to variant 1. The resulting protein (isoform 4) has a shorter N-terminus when compared to isoform 1, although the 31 most N-term aas are maintained. Isoform 4 is also known as the beta form. |

TABLE 3

DNA-Sequences (such as cDNA) corresponding to each of the isoforms

| SEQ ID NO. | Nucleotide Sequence | Description |
| --- | --- | --- |
| SEQ ID NO 5 | ATGCCTCACCTTATGGAAAGGATGGTGGGCTCTGGCCT<br>CCTGTGGCTGGCCTTGGTCTCCTGCATTCTGACCCAGG<br>CATCTGCAGTGCAGCGAGGTTATGGAAACCCCATTGAA<br>GCCAGTTCGTATGGGCTGGACCTGGACTGCGGAGCTCC<br>TGGCACCCCAGAGGCTCATGTCTGTTTTGACCCCTGTCA<br>GAATTACACCCTCCTGGATGAACCCTTCCGAAGCACAGA<br>GAACTCAGCAGGGTCCCAGGGGTGCGATAAAAACATGA<br>GCGGCTGGTACCGCTTTGTAGGGGAAGGAGGAGTAAGG<br>ATGTCGGAGACCTGTGTCCAGGTGCACCGATGCCAGAC<br>AGACGCTCCCATGTGGCTGAATGGGACCCACCCTGCCC<br>TTGGGGATGGCATCACCAACCACACTGCCTGTGCCCATT<br>GGAGTGGCAACTGCTGTTTCTGGAAAACAGAGGTGCTG<br>GTGAAGGCCTGCCCAGGCGGGTACCATGTGTACCGGTT<br>GGAAGGCACTCCCTGGTGTAATCTGAGATACTGCACAGT<br>TCCACGAGACCCATCCACTGTGGAGGACAAGTGTGAGA<br>AGGCCTGCCGCCCCGAGGAGGAGTGCCTTGCCCTCAAC<br>AGCACCTGGGGCTGTTTCTGCAGACAGGACCTCAATAG<br>TTCTGATGTCCACAGTTTGCAGCCTCAGCTAGACTGTGG<br>GCCCAGGGAGATCAAGGTGAAGGTGGACAAATGTTTGC<br>TGGGAGGCCTGGGTTTGGGGGAGGAGGTCATTGCCTAC<br>CTGCGAGACCCAAACTGCAGCAGCATCTTGCAGACAGA<br>GGAGAGGAACTGGGTATCTGTGACCAGCCCCGTCCAGG<br>CTAGTGCCTGCAGGAACATTCTGGAGAGAAATCAAACCC<br>ATGCCATCTACAAAAACACCCTCTCCTTGGTCAATGATTT<br>CATCATCAGAGACACCATCCTCAACATCAACTTCCAATG<br>TGCCTACCCACTGGACATGAAAGTCAGCCTCCAAGCTG<br>CCTTGCAGCCCATTGTAAGTTCCCTGAACGTCAGTGTGG<br>ACGGGAATGGAGAGTTCATTGTCAGGATGGCCCTCTTC<br>CAAGACCAGAACTACACGAATCCTTACGAAGGGGATGC<br>AGTTGAACTGTCTGTTGAGTCCGTGCTGTATGTGGGTGC<br>CATCTTGGAACAAGGGGACACCTCCCGGTTTAACCTGGT<br>GTTGAGGAACTGCTATGCCACCCCCACTGAAGACAAGG<br>CTGACCTTGTGAAGTATTTCATCATCAGAAACAGCTGCT<br>CAAATCAACGTGATTCCACCATCCACGTGGAGGAGAATG<br>GGCAGTCCTCGGAAAGCCGGTTCTCAGTTCAGATGTTCA<br>TGTTTGCTGGACATTATGACCTAGTTTTCCTGCATTGTGA<br>GATTCATCTCTGTGATTCTCTTAATGAACAGTGCCAGCCT<br>TCTTGCTCAAGAAGTCAAGTCCGCAGTGAAGTACCGGC<br>CATCGACCTAGCCCGGGTTCTAGATTTGGGGCCCATCA<br>CTCGGAGAGGTGCACAGTCTCCCGGTGTCATGAATGGA<br>ACCCCTAGCACTGCAGGGTTCCTGGTGGCCTGGCCTAT<br>GGTCCTCCTGACTGTCCTCCTGGCTTGGCTGTTCTGA | Isoform 1<br>CCDS Database<br>CCDS42128.1 |
| SEQ ID NO 6 | ATGCCTCACCTTATGGAAAGGATGGTGGGCTCTGGCCT<br>CCTGTGGCTGGCCTTGGTCTCCTGCATTCTGACCCAGG<br>CATCTGCAGTGCAGCGAGGTTATGGAAACCCCATTGAA<br>GCCAGTTCGTATGGGCTGGACCTGGACTGCGGAGCTCC<br>TGGCACCCCAGAGGCTCATGTCTGTTTTGACCCCTGTCA<br>GAATTACACCCTCCTGGATGAACCCTTCCGAAGCACAGA | Isoform 2<br>CCDS Database<br>CCDS10582.2 |

TABLE 3-continued

DNA-Sequences (such as cDNA) corresponding to each of the isoforms

| SEQ ID NO. | Nucleotide Sequence | Description |
|---|---|---|
| | GAACTCAGCAGGGTCCCAGGGGTGCGATAAAAACATGA<br>GCGGCTGGTACCGCTTTGTAGGGGAAGGAGGAGTAAGG<br>ATGTCGGAGACCTGTGTCCAGGTGCACCGATGCCAGAC<br>AGACGCTCCCATGTGGCTGAATGGGACCCACCCTGCCC<br>TTGGGGATGGCATCACCAACCACACTGCCTGTGCCCATT<br>GGAGTGGCAACTGCTGTTTCTGGAAAACAGAGGTGCTG<br>GTGAAGGCCTGCCCAGGCGGGTACCATGTGTACCGGTT<br>GGAAGGCACTCCCTGGTGTAATCTGAGATACTGCACAG<br>ACCCATCCACTGTGGAGGACAAGTGTGAGAAGGCCTGC<br>CGCCCCGAGGAGGAGTGCCTTGCCCTCAACAGCACCTG<br>GGGCTGTTTCTGCAGACAGGACCTCAATAGTTCTGATGT<br>CCACAGTTTGCAGCCTCAGCTAGACTGTGGGCCCAGGG<br>AGATCAAGGTGAAGGTGGACAAATGTTTGCTGGGAGGC<br>CTGGGTTTGGGGGAGGAGGTCATTGCCTACCTGCGAGA<br>CCCAAACTGCAGCAGCATCTTGCAGACAGAGGAGAGGA<br>ACTGGGTATCTGTGACCAGCCCCGTCCAGGCTAGTGCC<br>TGCAGGAACATTCTGGAGAGAAATCAAACCCATGCCATC<br>TACAAAAACACCCTCTCCTTGGTCAATGATTTCATCATCA<br>GAGACACCATCCTCAACATCAACTTCCAATGTGCCTACC<br>CACTGGACATGAAAGTCAGCCTCCAAGCTGCCTTGCAG<br>CCCATTGTAAGTTCCCTGAACGTCAGTGTGGACGGGAAT<br>GGAGAGTTCATTGTCAGGATGGCCCTCTTCCAAGACCA<br>GAACTACACGAATCCTTACGAAGGGGATGCAGTTGAACT<br>GTCTGTTGAGTCCGTGCTGTATGTGGGTGCCATCTTGGA<br>ACAAGGGGACACCTCCCGGTTTAACCTGGTGTTGAGGA<br>ACTGCTATGCCACCCCCACTGAAGACAAGGCTGACCTT<br>GTGAAGTATTTCATCATCAGAAACAGCTGCTCAAATCAA<br>CGTGATTCCACCATCCACGTGGAGGAGAATGGGCAGTC<br>CTCGGAAAGCCGGTTCTCAGTTCAGATGTTCATGTTTGC<br>TGGACATTATGACCTAGTTTTCCTGCATTGTGAGATTCAT<br>CTCTGTGATTCTCTTAATGAACAGTGCCAGCCTTCTTGCT<br>CAAGAAGTCAAGTCCGCAGTGAAGTACCGGCCATCGAC<br>CTAGCCCGGGTTCTAGATTTGGGGCCCATCACTCGGAG<br>AGGTGCACAGTCTCCCGGTGTCATGAATGGAACCCCTA<br>GCACTGCAGGGTTCCTGGTGGCCTGGCCTATGGTCCTC<br>CTGACTGTCCTCCTGGCTTGGCTGTTCTGA | |
| SEQ ID NO 7 | ATGCCTCACCTTATGGAAAGGATGGTGGGCTCTGGCCT<br>CCTGTGGCTGGCCTTGGTCTCCTGCATTCTGACCCAGG<br>CATCTGCAGTGCAGCGAGTTCCACGAGACCCATCCACT<br>GTGGAGGACAAGTGTGAGAAGGCCTGCCGCCCCGAGG<br>AGGAGTGCCTTGCCCTCAACAGCACCTGGGCTGTTTC<br>TGCAGACAGGACCTCAATAGTTCTGATGTCCACAGTTTG<br>CAGCCTCAGCTAGACTGTGGGCCCAGGGAGATCAAGGT<br>GAAGGTGGACAAATGTTTGCTGGGAGGCCTGGGTTTGG<br>GGGAGGAGGTCATTGCCTACCTGCGAGACCCAAACTGC<br>AGCAGCATCTTGCAGACAGAGGAGAGGAACTGGGTATC<br>TGTGACCAGCCCCGTCCAGGCTAGTGCCTGCAGGAACA<br>TTCTGGAGAGAAATCAAACCCATGCCATCTACAAAAACA<br>CCCTCTCCTTGGTCAATGATTTCATCATCAGAGACACCA<br>TCCTCAACATCAACTTCCAATGTGCCTACCCACTGGACA<br>TGAAAGTCAGCCTCCAAGCTGCCTTGCAGCCCATTGTAA<br>GTTCCCTGAACGTCAGTGTGGACGGGAATGGAGAGTTC<br>ATTGTCAGGATGGCCCTCTTCCAAGACCAGAACTACACG<br>AATCCTTACGAAGGGGATGCAGTTGAACTGTCTGTTGAG<br>TCCGTGCTGTATGTGGGTGCCATCTTGGAACAAGGGGA<br>CACCTCCCGGTTTAACCTGGTGTTGAGGAACTGCTATGC<br>CACCCCCACTGAAGACAAGGCTGACCTTGTGAAGTATTT<br>CATCATCAGAAACAGCTGCTCAAATCAACGTGATTCCAC<br>CATCCACGTGGAGGAGAATGGGCAGTCCTCGGAAAGCC<br>GGTTCTCAGTTCAGATGTTCATGTTTGCTGGACATTATGA<br>CCTAGTTTTCCTGCATTGTGAGATTCATCTCTGTGATTCT<br>CTTAATGAACAGTGCCAGCCTTCTTGCTCAAGAAGTCAA<br>GTCCGCAGTGAAGTACCGGCCATCGACCTAGCCCGGGT<br>TCTAGATTTGGGGCCCATCACTCGGAGAGGTGCACAGT<br>CTCCCGGTGTCATGAATGGAACCCCTAGCACTGCAGGG<br>TTCCTGGTGGCCTGGCCTATGGTCCTCCTGACTGTCCTC<br>CTGGCTTGGCTGTTCTGA | Isoform 3<br>CCDS Database<br>CCDS45433.1 |
| SEQ ID NO 8 | ATGCCTCACCTTATGGAAAGGATGGTGGGCTCTGGCCT<br>CCTGTGGCTGGCCTTGGTCTCCTGCATTCTGACCCAGG<br>CATCTGCAGTGCAGCGAGACCCATCCACTGTGGAGGAC<br>AAGTGTGAGAAGGCCTGCCGCCCCGAGGAGGAGTGCC<br>TTGCCCTCAACAGCACCTGGGCTGTTTCTGCAGACAG<br>GACCTCAATAGTTCTGATGTCCACAGTTTGCAGCCTCAG<br>CTAGACTGTGGGCCCAGGGAGATCAAGGTGAAGGTGGA | Isoform 4<br>CCDS Database<br>CCDS45432.1 |

TABLE 3-continued

DNA-Sequences (such as cDNA) corresponding to each of the isoforms

| SEQ ID NO. | Nucleotide Sequence | Description |
|---|---|---|
| | CAAATGTTTGCTGGGAGGCCTGGGTTTGGGGGAGGAGG<br>TCATTGCCTACCTGCGAGACCCAAACTGCAGCAGCATCT<br>TGCAGACAGAGGAGAGGAACTGGGTATCTGTGACCAGC<br>CCCGTCCAGGCTAGTGCCTGCAGGAACATTCTGGAGAG<br>AAATCAAACCCATGCCATCTACAAAAACACCCTCTCCTT<br>GGTCAATGATTTCATCATCAGAGACACCATCCTCAACAT<br>CAACTTCCAATGTGCCTACCCACTGGACATGAAAGTCAG<br>CCTCCAAGCTGCCTTGCAGCCCATTGTAAGTTCCCTGAA<br>CGTCAGTGTGGACGGGAATGGAGAGTTCATTGTCAGGA<br>TGGCCCTCTTCCAAGACCAGAACTACACGAATCCTTACG<br>AAGGGGATGCAGTTGAACTGTCTGTTGAGTCCGTGCTGT<br>ATGTGGGTGCCATCTTGGAACAAGGGGACACCTCCCGG<br>TTTAACCTGGTGTTGAGGAACTGCTATGCCACCCCCACT<br>GAAGACAAGGCTGACCTTGTGAAGTATTTCATCATCAGA<br>AACAGCTGCTCAAATCAACGTGATTCCACCATCCACGTG<br>GAGGAGAATGGGCAGTCCTCGGAAAGCCGGTTCTCAGT<br>TCAGATGTTCATGTTTGCTGGACATTATGACCTAGTTTTC<br>CTGCATTGTGAGATTCATCTCTGTGATTCTCTTAATGAAC<br>AGTGCCAGCCTTCTTGCTCAAGAAGTCAAGTCCGCAGTG<br>AAGTACCGGCCATCGACCTAGCCCGGGTTCTAGATTTG<br>GGGCCCATCACTCGGAGAGGTGCACAGTCTCCCGGTGT<br>CATGAATGGAACCCCTAGCACTGCAGGGTTCCTGGTGG<br>CCTGGCCTATGGTCCTCCTGACTGTCCTCCTGGCTTGG<br>CTGTTCTGA | |

The CCDS reference refers to the CCDS project as described in "The consensus coding sequence (CCDS) project: Identifying a common protein-coding gene set for the human and mouse genomes", Pruitt K D, et al, Genome Res. 2009 July; 19(7):1316-23.

An autoantibody is an antibody (a type of protein) manufactured by the immune system that is directed against one or more of the individual's own proteins. Many autoimmune diseases are associated with and/or caused by such autoantibodies.

The term "autoimmune disease" refers to any given disease associated with and/or caused by the presence of autoantibodies. Autoimmune diseases arise from an abnormal immune response of the body against substances and tissues normally present in the body (autoimmunity). This may be restricted to certain organs or involve a particular tissue.

A preferred autoimmune disease of the invention is inflammatory bowel disease. The term "inflammatory bowel disease" or "IBD" refers to gastrointestinal disorders including, without limitation, Crohn's disease (CD), ulcerative colitis (UC), and indeterminate colitis (IC).

A preferred autoimmune disease of the invention is therefore an autoimmune disease of the digestive or intestinal tract of said subject. Such diseases are characterized in that the autoimmune disorder exhibits autoantibodies that bind components of the digestive or intestinal tract of said subject. Such components of the digestive or intestinal tract may be any organ, tissue, cell or protein found in said area of the subject. The digestive or intestinal tract may be understood as the gastrointestinal tract (GI tract), which refers to the stomach and intestine, and is divided into the upper and lower gastrointestinal tracts, and may include all the structures from the mouth to the anus. The tract may also be divided into foregut, midgut, and hindgut, reflecting the embryological origin of each segment of the tract.

Gastrointestinal (GI)-related autoantibodies (Abs) can be evaluated in autoimmune diseases such as inflammatory bowel disease, autoimmune hepatitis and celiac disease. Such autoantibodies may relate to ANCA (anti-neutrophil cytoplasmic antibodies) and/or ASCA. IgA and IgG ASCA can be detected in sera from patients with Crohn's disease and may be used in order to differentiate Crohn's disease from UC.

The term "sample" includes any biological specimen obtained from an individual. Suitable samples for use in the present invention include, without limitation, whole blood, plasma, serum, saliva, urine, stool, tears, any other bodily fluid, pure pancreatic juices or duodenal juices, tissue samples (e.g., biopsy) and cellular extracts thereof (e.g., red blood cellular extract). In a preferred embodiment, the sample is a serum sample. The use of samples such as serum, saliva, and urine is well known in the art (see, e.g., Hashida et al., J. Clin. Lab. Anal., 11:267-86 (1997)). One skilled in the art will appreciate that samples such as serum samples can be diluted prior to analysis.

The term "individual," "subject," or "patient" typically refers to humans, but also to other animals including, e.g., other primates, rodents, canines, felines, equines, ovines, porcines, and the like.

As used herein, the term "substantially the same amino acid sequence" includes an amino acid sequence that is similar, but not identical to, the naturally-occurring amino acid sequence. For example, an amino acid sequence, i.e., polypeptide, that has substantially the same amino acid sequence as the GP2 isoforms in SEQ ID NO 1 to 4 and can have one or more modifications such as amino acid additions, deletions, or substitutions relative to the amino acid sequence of the GP2 isoforms, provided that the modified polypeptide retains substantially at least one biological activity of GP2 such as immunoreactivity, in particular the immune reactivity specific to the diseases capable of being diagnosed according to the present invention. A particularly useful modification of a polypeptide of the present invention, or a fragment thereof, is a modification that confers, for example, increased stability or reactivity. Incorporation of one or more D-amino acids is a modification useful in increasing stability of a polypeptide or polypeptide fragment. Similarly, deletion or substitution of lysine residues can increase stability by protecting the polypeptide or polypeptide fragment against degradation.

As used herein, the term "GP2 isoform" includes a protein that has at least about 50% amino acid identity with one or more SEQ ID No 1 to 4. As a non-limiting example, an GP2 isoform of the invention can have at least about 60%, 65%, 70%, 75%, 80%, 85%, 90%, 91%, 92%, 93%, 94%, 95%, 96%, 97%, 98%, or 99% amino acid sequence identity with one or more SEQ ID No 1 to 4. Nucleic acid variants to SEQ ID NO 5 to 8 are also encompassed herein that encode a protein sequence of SEQ ID NO 1 to 4, or a sequence with substantially the same amino acid sequence. The complementary nucleic acid sequence is also encompassed, as is a degenerate sequence modified to use the degenerate nature of the genetic code, as is known to a skilled person.

The amino acid sequences may also comprise 0 to 100, 2 to 50, 5 to 20, or for example 8 to 15, or any value from 0 to 20, amino acid additions or deletions at either the N- and/or C-terminus of the proteins. The termini may also be modified with additional linker sequences, or removal of sequences, as long as the autoantibody binding properties and immunoreactivity of the protein is essentially maintained and the autoantibodies as described herein bind in an analogous manner to the specific sequence provided.

Various ways of preparing functionally analogous peptides have been disclosed in the prior art. Peptides designed starting from the peptides of the invention using such methods are included in the teaching according to the invention. For example, one way of generating functionally analogous peptides has been described in PNAS USA 1998, Oct. 13, 9521, 12179-84; WO 99/6293 (U.S. Pat. No. 6,316,511) and/or WO 02/38592 (U.S. Pat. No. 7,205,382), which are incorporated herein by reference in their entirety. That is, all peptides, peptide fragments or structures comprising peptides generated using the methods mentioned above—starting from the peptides of the invention—are peptides according to the invention, provided they accomplish the object of the invention and, in particular, interact with the pathogenic auto-antibodies. For example, these autoantibodies can be agonistic autoantibodies activating receptors.

The GP2 isoforms may also be described as antigens, as they react with an antibody targeted to said GP2 isoform protein. The GP2 isoforms may also be referred to as proteins or targets. For use in the methods of the invention, a GP2 antigen can be partially purified. A GP2 antigen also can be prepared recombinantly by expressing an encoding nucleic acid sequence as described herein using methods well known in the art (see, for example, Ausubel et al., Current Protocols in Molecular Biology John Wiley & Sons, Inc. New York (1999)).

The term "diagnosing" includes the use of the devices, methods, and systems, of the present invention to determine the presence or absence or likelihood of presence or absence of a medically relevant disorder in an individual. The term also includes devices, methods, and systems for assessing the level of disease activity in an individual. In some embodiments, statistical algorithms are used to diagnose a mild, moderate, severe, or fulminant form of the disorder based upon the criteria developed by Truelove et al., Br. Med. J., 12:1041-1048 (1955). In other embodiments, statistical algorithms are used to diagnose a mild to moderate, moderate to severe, or severe to fulminant form of the IBD based upon the criteria developed by Hanauer et al., Am. J. Gastroenterol., 92:559-566 (1997). In other embodiments, the presence of GP2 antibodies is used to diagnose Crohn's disease. One skilled in the art will know of other methods for evaluating the severity of IBD in an individual.

The comparative analysis described herein between autoantibody binding to different GP2 isoforms is a preferred method of the present invention. Direct comparison based on auto-antibody binding as measured in the same experiment may be used. For this embodiment the amount of GP2 isoform provided for the experiment should be controlled carefully to enable direct comparative analysis. Alternatively, or in combination, control values or standards may be used that provide samples with autoantibodies or represent control amounts thereof, as have already been obtained from previous analytical tests. It is possible to use control values having been generated by the testing of cohorts or other large numbers of subjects suffering from any given disease or control group. Appropriate statistical means are known to those skilled in the art for analysis and comparison of such data sets. Control samples for positive controls (such as disease sufferers) or negative controls (from healthy subjects) may be used for reference values in either simultaneous of non-simultaneous comparison.

The invention also encompasses use of the method for disease monitoring, also known as monitoring the progression or regression of the autoimmune disease. The term "monitoring the progression or regression of the autoimmune disease" includes the use of the devices, methods, and systems of the present invention to determine the disease state (e.g., presence or severity of the autoimmune disease) of an individual. In certain instances, the results of a statistical algorithm (e.g., a learning statistical classifier system) are compared to those results obtained for the same individual at an earlier time. In some aspects, the devices, methods, and systems of the present invention can also be used to predict the progression of the autoimmune disease, e.g., by determining a likelihood for the autoimmune disease to progress either rapidly or slowly in an individual based on the presence or level of at least one marker in a sample. In other aspects, the devices, methods, and systems of the present invention can also be used to predict the regression of the autoimmune disease, e.g., by determining a likelihood for the autoimmune disease to regress either rapidly or slowly in an individual based on the presence or level of at least one marker in a sample. Therapy monitoring may also be conducted, whereby a subject is monitored for disease progression during the course of any given therapy.

In certain instances, the presence or level of anti-GP2 antibodies or at least one marker is determined using an immunoassay or an immunohistochemical assay. A non-limiting example of an immunoassay suitable for use in the method of the present invention includes an ELISA. Examples of immunohistochemical assays suitable for use in the method of the present invention include, but are not limited to, immunofluorescence assays such as direct fluorescent antibody assays, IFA assays, anticomplement immunofluorescence assays, and avidin-biotin immunofluorescence assays. Other types of immunohistochemical assays include immunoperoxidase assays.

Celiac disease (CeD) is an autoimmune disorder of the small intestine that occurs in people of all ages from infancy onward. Symptoms include discomfort in the digestive tract, chronic constipation and diarrhea, anemia and fatigue, but these may be absent, and symptoms in other organ systems have been described. Severe CeD leads to the characteristic symptoms of pale, loose and greasy stool (steatorrhea) and weight loss or failure to gain weight (in young children). People with milder coeliac disease may have symptoms that are much more subtle and occur in other organs than the bowel itself. It is also possible to have coeliac disease without any symptoms whatsoever. Abdominal pain and cramping, bloatedness with abdominal distension and mouth ulcers may be present. As the bowel becomes more damaged, a degree of lactose intolerance may develop. Frequently, the symptoms are ascribed to irritable bowel syndrome (IBS), only later to be recognized as coeliac disease; a small proportion of people with symptoms of IBS have underlying coeliac disease, and screening for coeliac disease is recommended for those with IBS symptoms.

Crohn's disease (CD) is a disease of chronic inflammation that can involve any part of the gastrointestinal tract. Commonly, the distal portion of the small intestine, i.e., the ileum, and the cecum are affected. In other cases, the disease is confined to the small intestine, colon, or anorectal region. CD occasionally involves the duodenum and stomach, and more rarely the esophagus and oral cavity. The variable clinical manifestations of CD are, in part, a result of the varying anatomic localization of the disease. The most frequent symptoms of CD are abdominal pain, diarrhea, and recurrent fever. CD is commonly associated with intestinal obstruction or fistula, an abnormal passage between diseased loops of bowel.

Crohn's disease belongs to the group of chronic inflammatory bowel diseases. It is a presumably autoaggressive, chronic-granulomatous inflammation which may appear in the entire gastrointestinal tract, i.e. from the oral cavity down to the anus. Affection is mainly in the lower small intestine (terminal ileum, affection about 40%) and colon, more rarely in esophagus and mouth. Crohn's disease is characterized by a discontinuous, segmental affection (so-called "skip lesions") of the intestinal mucosa, i.e., the disease can be present simultaneously in a plurality of intestinal sections separated by healthy sections. Other designations of the disease are regional enteritis, terminal ileitis, regional enterocolitis and sclerosing chronic enteritis, or the abbreviation CD (Crohn's disease), and the autoimmune disease (inflammatory bowel disease) as a generic term. Accordingly, Crohn's disease in the meaning of the invention is any condition which is macroscopically characterized by the following changes: Garden hose phenomenon: segmental stenoses caused by fibrosing, Cobble stone phenomenon: inflamed mucosa in alternation with deep ulcerations, thereby producing a cobble stone-like appearance, or Inflammatory conglomerate tumor: various intestinal sections adhere to each other.

Ulcerative colitis (UC) is a disease of the large intestine characterized by chronic diarrhea with cramping, abdominal pain, rectal bleeding, loose discharges of blood, pus, and mucus.

The manifestations of UC vary widely. A pattern of exacerbations and remissions typifies the clinical course for about 70% of UC patients, although continuous symptoms without remission are present in some patients with UC. Local and systemic complications of UC include arthritis, eye inflammation such as uveitis, skin ulcers, and liver disease. In addition, UC, and especially the long-standing, extensive form of the disease is associated with an increased risk of colon carcinoma.

In another preferred embodiment of the invention the inflammatory bowel disease is Crohn's disease, chronic pancreatitis and/or ulcerative colitis. To date, detection or differentiation of the above diseases was only possible with limited success or great efforts. The above preferred embodiment now enables easy detection of Crohn's disease and chronic pancreatitis and even differentiation from ulcerative colitis by means of differential diagnostics.

Pancreatitis in the meaning of the invention is inflammation of the pancreas which can be acute or take a chronic course. Pancreatitis is usually induced by activation of pancreatic enzymes within the organ. The function of these enzymes is to digest proteins and fat so that autodigestion of the organ is induced. Autodigestion results in inflammation of the pancreas. In severe cases, hemorrhage, serious tissue damage, infections and cysts may develop. An inflamed gland may cause enzymes to enter the bloodstream, thus reaching the lungs, heart and kidneys where further damage may arise. Acute pancreatitis develops when the pancreas suddenly becomes inflamed but recovers afterwards. Some patients suffer from acute pancreatitis a number of times but recover completely each time. Acute pancreatitis appears suddenly and can be a serious, life-threatening disease causing a large number of complications, but the patients normally recover from acute pancreatitis. The incidence is about five to ten new diseases per 100,000 inhabitants per year.

In another preferred embodiment of the invention, the GP2 isoforms described herein are used to detect hepatic diseases, primary sclerosing cholangitis and/or autoimmune enteritides. Most surprisingly, the GP2 autoantigen is suitable not only for specific detection of the autoimmune disease, but also for the detection of various hepatic diseases.

Cholangitis in the meaning of the invention refers to inflammation of the intrahepatic biliary ducts. It can be induced by various causes, including—among other things—obstruction of the biliary ducts by gallstones, stenoses, tumors or parasite infestation. It is differentiated into acute purulent cholangitis, non-purulent destructive cholangitis and chronic sclerosing cholangitis.

Autoimmune enteritides in the meaning of the invention involve any form of enteritis, especially those being caused by chronic inflammatory bowel diseases. Also, autoimmune enteritides in the meaning of the invention involve those being caused by *salmonella, E. coli, cholera* or typhus pathogens, or by fungi, protozoa, toxic substances, but also any allergy-based enteritis or any form of actinic enteritis, Yersinia enteritis or bacterial dysentery.

As used herein, the term "antibody" includes a population of immunoglobulin molecules, which can be polyclonal or monoclonal and of any isotype, or an immunologically active fragment of an immunoglobulin molecule. Such an immunologically active fragment contains the heavy and light chain variable regions, which make up the portion of the antibody molecule that specifically binds an antigen. For example, an immunologically active fragment of an immunoglobulin molecule known in the art as Fab, Fab' or F(ab')2 is included within the meaning of the term antibody.

In another advantageous embodiment the immunoassay is used in the detection of antibodies, to which end binding of the GP2 isoform antigen to a solid phase is envisaged. Following addition of sample solution, the patients antibody included therein binds to the GP2 antigen. The antibody which is obtained e.g. from the serum or stool of a patient and bound to GP2 is subsequently detected using a label, or labelled reagent and optionally quantified. Thus, according to the invention, detection of the antibodies in this method is effected using labelled reagents according to the well-known ELISA (Enzyme-Linked Immunosorbent Assay) technology. Labels according to the invention therefore comprise enzymes catalyzing a chemical reaction which can be determined by optical means, especially by means of chromogenic substrates, chemiluminescent methods or fluorescent dyes. In another preferred embodiment the autoantibodies are detected by labelling with weakly radio-active substances in radioimmunoassays (RIA) wherein the resulting radioactivity is measured.

As examples of means for detecting the label in the method of the present invention, a variety of immunoassay techniques, including competitive and non-competitive immunoassays, can be used to determine the presence or level of one or more markers in a sample (see, e.g., Self et al., Curr. Opin. Biotechnol., 7:60-65 (1996)). The term immunoassay encompasses techniques including, without limitation, enzyme immunoassays (EIA) such as enzyme multiplied immunoassay technique (EMIT), enzyme-linked immunosorbent assay (ELISA), antigen capture ELISA, sandwich ELISA, IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence (see, e.g., Schmalzing et al., Electrophoresis, 18:2184-2193 (1997); Bao, J. Chromatogr. B. Biomed. Sci., 699:463-480 (1997)). Liposome immunoassays, such as flow-injection liposome immunoassays and liposome immunosensors, are also suitable for use in the present invention (see, e.g., Rongen et al., J. Immunol. Methods, 204:105-133 (1997)). In addition, nephelometry assays, in which the formation of protein/antibody complexes results in increased light scatter that is converted to a peak rate signal as a function of the marker concentration, are suitable for use in the present invention. Nephelometry assays are commercially available from Beckman Coulter (Brea, Calif.; Kit #449430) and can be performed using a Behring Nephelometer Analyzer (Fink et al., J. Clin. Chem. Clin. Biol. Chem., 27:261-276 (1989)).

The immunoassays described above are particularly useful for determining the presence or level of one or more markers in a sample (and may be considered examples of means for detecting a label), wherein a marker may be understood as an autoantibody targeted to an isoform of GP2. As a non-limiting example, a fixed neutrophil ELISA is useful for determining whether a sample is positive for ANCA or for determining ANCA levels in a sample. Similarly, an ELISA using yeast cell wall phosphopeptidomannan is useful for determining whether a sample is positive for ASCA-IgA and/or ASCA-IgG, or for determining ASCA-IgA and/or ASCA-IgG levels in a sample. An ELISA using GP2 isoform protein or a fragment thereof is useful for determining whether a sample is positive for anti-GP2 antibodies, or for determining anti-GP2 antibody levels in a sample.

In another preferred embodiment of the method according to the invention the autoantibodies are detected in an immunoassay, preferably with direct or indirect coupling of one reactant to a labelling substance. This enables flexible adaptation of the method to the potentials and requirements of different laboratories and their laboratory diagnostic equipment. In one advantageous embodiment the autoimmune disease-specific antibodies are detected in an immunoassay wherein the antibodies are present dissolved in a liquid phase, preferably diluted in a conventional buffer solution well-known to those skilled in the art or in an undiluted body fluid. According to the invention, detection can also be effected using stool samples.

In another preferred embodiment of the invention, soluble or solid phase-bound GP2 molecules are used to bind the antibodies. In a second reaction step, anti-human immunoglobulins are employed, preferably selected from the group comprising anti-human IgA, anti-human IgM and/or anti-human IgG antibodies, said anti-human immunoglobulins being detectably labelled conjugates of two components which can be conjugated with any conventional labelling enzymes, especially chromogenic and/or chemiluminescent substrates, preferably with horseradish peroxidase, alkaline phosphatase. The advantage of this embodiment lies in the use of ELISA technology usually available in laboratory facilities so that detection according to the invention can be established in a cost-effective manner. In another preferred embodiment of the invention the antibody bound to GP2 reacts with anti-human immunoglobulins, preferably selected from the group comprising anti-human IgA, anti-human IgM and/or anti-human IgG antibodies, detectably coupled to fluorescein isothiocyanate (FITC). Much like the above-mentioned ELISA, the FITC technology represents a system that is available in many places and therefore allows smooth and low-cost establishment of the inventive detection in laboratory routine.

Specific immunological binding of the antibody to the marker of interest can be detected directly or indirectly via a label. Any given means for detecting these labels may be considered means for detecting the label according to the method of the invention. Direct labels include fluorescent or luminescent tags, metals, dyes, radionuclides, and the like, attached to the antibody. An antibody labeled with iodine-125 (125I) can be used for determining the levels of one or more markers in a sample. A chemiluminescence assay using a chemiluminescent antibody specific for the marker is suitable for sensitive, non-radioactive detection of marker levels. An antibody labeled with fluorochrome is also suitable for determining the levels of one or more markers in a sample. Examples of fluorochromes include, without limitation, DAPI, fluorescein, Hoechst 33258, R-phycocyanin, B-phycoerythrin, R-phycoerythrin, rhodamine, Texas red, and lissamine. Secondary antibodies linked to fluorochromes can be obtained commercially, e.g., goat F(ab')2 anti-human IgG-FITC is available from Tago Immunologicals (Burlingame, Calif.).

Indirect labels include various enzymes well-known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm.

A signal from the direct or indirect label can be analyzed, for example, using a spectrophotometer to detect color from a chromogenic substrate; a radiation counter to detect radiation such as a gamma counter for detection of 125I; or a fluorometer to detect fluorescence in the presence of light of a certain wavelength. For detection of enzyme-linked antibodies, a quantitative analysis of the amount of marker levels can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

In certain embodiments, the present invention provides methods of diagnosing the autoimmune disease or clinical subtypes thereof using GP2 isoforms. A variety of inflammatory bowel disease (the autoimmune disease) markers, such as biochemical markers, serological markers, genetic markers, or other clinical or echographic characteristics, are suitable for use and can be combined with statistical algorithms to classify a sample from an individual as an the autoimmune disease sample. Examples of markers of the diseases (an autoantibody directed against the GP2 isoforms described herein) suitable for use in the present invention include, but are not limited to, anti-neutrophil antibodies (e.g., ANCA, pANCA, cANCA, NSNA, SAPPA, etc.) or anti-*Saccharomyces cerevisiae* antibodies (e.g., ASCA-IgA, ASCA-IgG, ASCA-IgM, etc.). One skilled in the art will know of additional markers suitable for use in the statistical algorithms of the present invention.

The determination of ANCA levels and/or the presence or absence of pANCA in a sample is useful in the present invention. As used herein, the term "anti-neutrophil cytoplasmic antibody" or "ANCA" includes antibodies directed to cytoplasmic and/or nuclear components of neutrophils. ANCA activity can be divided into several broad categories based upon the ANCA staining pattern in neutrophils: (1) cytoplasmic neutrophil staining without peri-nuclear highlighting (cANCA); (2) perinuclear staining around the outside edge of the nucleus (pANCA); (3) perinuclear staining around the inside edge of the nucleus (NSNA); and (4) diffuse staining with speckling across the entire neutrophil (SAPPA). ANCA levels in a sample from an individual can be determined, for example, using an immunoassay such as an enzyme-linked immunosorbent assay (ELISA) with alcohol-fixed neutrophils.

The determination of ASCA (e.g., ASCA-IgA and/or ASCA-IgG) levels in a sample is also useful in the present invention. As used herein, the term "anti-*Saccharomyces cerevisiae* immunoglobulin A" or "ASCA-IgA" includes antibodies of the immunoglobulin A isotype that react specifically with *S. cerevisiae*. Similarly, the term "anti-Saccharomyces cerevisiae immunoglobulin G" or "ASCA-IgG" includes antibodies of the immunoglobulin G isotype that react specifically with *S. cerevisiae*. The determination of whether a sample is positive for ASCA-IgA or ASCA-IgG is made using an antigen specific for ASCA. Such an antigen can be any antigen or mixture of antigens that is bound specifically by ASCA-IgA and/or ASCA-IgG. Although ASCA antibodies were initially characterized by their ability to bind *S. cerevisiae*, those of skill in the art will understand that an antigen that is bound specifically by ASCA can be obtained from S. cerevisiae or from a variety of other sources as long as the antigen is capable of binding specifically to ASCA antibodies.

The invention also relates to protein and nucleic acid molecules corresponding to the sequences described herein, for example proteins or nucleic acid molecules comprising or consisting of said sequences.

The determination of autoantibodies to the novel GP2-isoforms or use thereof in an ELISA as a solid-phase antigen in serological diagnostics of the diseases described herein has neither been considered nor mentioned in the prior art.

In another aspect, the invention relates to a method wherein human IgA, IgM and/or IgG antibody autoimmune diseases are detected.

As used herein, the term "GP2 isoform", "GP2", "GP2-antigen", "GP2-molecule", "GP2-protein", "GP2-peptide" or "GP2-autoantigen", or other GP2-referencing phrase relates to the novel GP2-isoforms of the sequences as disclosed herein, or functionally analogous sequences thereof, preferably to those isoforms 1, 2, 3 and 4. In a preferred embodiment of the method according to the invention the GP2-isoform is of human, animal, recombinant or synthetic origin. GP2 represents a highly conserved peptide so that GP2 of any origin can advantageously be used for detection as long as the sequence is functionally analog to the sequence according to the invention. High binding affinity between the GP2 as antigen and the autoantibodies is retained.

In another preferred embodiment of the invention the GP2 in accordance with one or more of the sequences disclosed herein is bound to a solid phase. Binding of GP2 in accordance with one or more of the sequences disclosed herein to the solid phase can be effected via a spacer. All those chemical compounds having suitable structural and functional preconditions for spacer function can be used as spacers as long as they do not modify the binding behavior in such a way that binding of the GP2 autoantibody in accordance with one or more of the sequences disclosed herein is adversely affected.

In another preferred embodiment of the invention the molecule comprises a linker or spacer selected from the group of α-aminocarboxylic acids as well as homo- and heterooligomers thereof, α,ω-aminocarboxylic acids and branched homo- or heterooligomers thereof, other amino acids, as well as linear and branched homo- or heterooligomers; amino-oligoalkoxy-alkylamines; maleinimidocarboxylic acid derivatives; oligomers of alkylamines; 4-alkylphenyl derivatives; 4-oligoalkoxyphenyl or 4-oligoalkoxyphenoxy derivatives; 4-oligoalkylmercaptophenyl or 4-oligoalkylmercaptophenoxy derivatives; 4-oligoalkylaminophenyl or 4-oligoalkylaminophenoxy derivatives; (oligoalkylbenzyl)phenyl or 4-(oligoalkylbenzyl) phenoxy derivatives, as well as 4-(oligoalkoxybenzyl) phenyl or 4-(oligoalkoxybenzyl)phenoxy derivatives; trityl derivatives; benzyloxyaryl or benzyloxyalkyl derivatives; xanthen-3-yloxy-alkyl derivatives; (4-alkylphenyl)- or ω-(4-alkylphenoxy)alkanoic acid derivatives; oligoalkylphenoxyalkyl or oligoalkoxyphenoxyalkyl derivatives; carbamate derivatives; amines; tri-alkylsilyl or dialkylalkoxysilyl derivatives; alkyl or aryl derivatives or combinations thereof.

According to the invention it is also preferred to perform the above-described detection method on a solid phase, for example by connection of the GP2 molecule to the solid phase via a linker, in which case the storability of the peptide is advantageously increased as a result of the surprisingly stable linkage of the GP2 antigen to the solid phase.

In another preferred embodiment of the invention the GP2 molecule is used as a soluble or solid phase-bound autoantigen for direct or indirect autoantibody detection in stool and/or body fluids, especially blood and/or serum, in which case the use of the GP2 molecule in accordance with one or more of the sequences as disclosed herein was found particularly advantageous.

In another preferred embodiment of the invention the sequences according to the present application, or the peptides which can be generated therefrom, are immobilized. More specifically, the solid phase-bound GP2 molecule in accordance with one or more of the sequences as disclosed herein is bound to organic, inorganic, synthetic and/or mixed polymers, preferably agarose, cellulose, silica gel, polyamides and/or polyvinyl alcohols. In the meaning of the invention, immobilization is understood to involve various methods and techniques to fix the peptides on specific carriers, e.g. according to WO 99/56126 or WO 02/26292.

For example, immobilization can serve to stabilize the peptides so that their activity would not be reduced or adversely modified by biological, chemical or physical exposure, especially during storage or in single-batch use. Immobilization of the peptides allows repeated use under technical or clinical routine conditions; furthermore, a sample—preferably blood components—can be reacted with at least one of the peptides according to the invention in a continuous fashion. In particular, this can be achieved by means of various immobilization techniques, with binding of the peptides to other peptides or molecules or to a carrier proceeding in such a way that the three-dimensional structure—particularly in the active center mediating the interaction with the autoantibodies—of the corresponding molecules, especially of said peptides, would not be changed. Advantageously, there is no loss in specificity to the autoantibodies of patients as a result of such immobilization. In the meaning of the invention, three basic methods can be used for immobilization:

(i) Crosslinking: in crosslinking, the peptides are fixed to one another without adversely affecting their activity. Advantageously, they are no longer soluble as a result of such cross-linking.

(ii) Binding to a carrier: binding to a carrier proceeds via adsorption, ionic binding or covalent binding, for example. Such binding may also take place inside microbial cells or liposomes or other membranous, closed or open structures. Advantageously, the peptides are not adversely affected by such fixing. For example, multiple or continuous use of carrier-bound peptides is possible with advantage in clinical diagnosis or therapy.

(iii) Inclusion: inclusion in the meaning of the invention especially proceeds in a semipermeable membrane in the form of gels, fibrils or fibers. Advantageously, encapsulated peptides are separated from the surrounding sample solution by a semipermeable membrane in such a way that interaction with the autoantibodies or fragments thereof still is possible. Various methods are available for immobilization, such as adsorption on an inert or electrically charged inorganic or organic carrier. For example, such carriers can be porous gels, aluminum oxide, bentonite, agarose, starch, nylon or polyacrylamide. Immobilization proceeds via physical binding forces, frequently involving hydrophobic interactions and ionic binding. Advantageously, such methods are easy to handle and have little influence on the conformation of the peptides. Advantageously, binding can be improved as a result of electrostatic binding forces between the charged groups of the peptides and the carrier, e.g. by using ion exchangers, particularly Sephadex.

Another method is covalent binding to carrier materials. In addition, the carriers may have reactive groups forming homopolar bonds with amino acid side chains. Suitable groups in peptides are carboxy, hydroxy and sulfide groups and especially the terminal amino groups of lysines. Aromatic groups offer the possibility of diazo coupling. The surface of microscopic porous glass particles can be activated by treatment with silanes and subsequently reacted with peptides. For example, hydroxy groups of natural polymers can be activated with bromocyanogen and subsequently coupled with peptides. Advantageously, a large number of peptides can undergo direct covalent binding with polyacrylamide resins. Inclusion in three-dimensional networks involves inclusion of the peptides in ionotropic gels or other structures well-known to those skilled in the art. More specifically, the pores of the matrix are such in nature that the peptides are retained, allowing interaction with the target molecules. In crosslinking, the peptides are converted into polymer aggregates by cross-linking with bifunctional agents. Such structures are gelatinous, easily deformable and, in particular, suitable for use in various reactors. By adding other inactive components such as gelatin in cross-linking, advantageous improvement of mechanical and binding properties is possible. In microencapsulation, the reaction volume of the peptides is restricted by means of membranes. For example, microencapsulation can be carried out in the form of an interfacial polymerization. Owing to the immobilization during microencapsulation, the peptides are made insoluble and thus reusable. In the meaning of the invention, immobilized peptides are all those peptides being in a condition that allows reuse thereof. Restricting the mobility and solubility of the peptides by chemical, biological or physical means advantageously results in lower process cost, particularly when eliminating autoantibodies from blood components.

The invention also relates to a diagnostic kit for the determination of autoimmune diseases, comprising a GP2 isoform molecule in accordance with one or more of the sequences as disclosed herein. The diagnostic kit optionally includes instructions concerning combining the contents of the kit and/or providing a formulation for the detection of inflammatory bowel diseases, particularly Crohn's disease, chronic pancreatitis, celiac disease and/or ulcerative colitis. For example, the instruction can be in the form of an instruction leaflet or other medium providing the user with information as to the type of method wherein the substances mentioned are to be used. Obviously, the information need not necessarily be in the form of an instruction leaflet, and the information may also be imparted via the Internet, for example. To a patient, one advantageous effect of such a kit is, for instance, that he or she, without directly addressing a physician, can determine the actual state of a disease even during a journey and optionally adapt diet and activities accordingly.

EXAMPLES

Without intending to be limiting, the invention will be explained in more detail with reference to an example.

The experiments provided herein demonstrate that autoantibodies targeted to the longer isoforms of GP2 (1 and 2) can be used for the diagnosis of de-novo celiac disease and are characterized by better assay performance characteristics than autoantibodies in comparison to the shorter isoforms. Autoantibodies to the shorter isoforms of GP2, in particular isoform 4, can be used for the differential diagnosis of inflammatory bowel diseases and show a better differentiation of Crohn's disease and ulcerative colitis patients. The experiments provided herein further demonstrate that isoforms of GP2 (1 and/or 2 and 3 and/or 4) is an autoimmune mucosal target and can be used for the diagnosis of primary sclerosing cholangitis (PSC).

Materials

Expression of GP2 in *Spodoptera frugiperda* 9 cells

Figure 1:
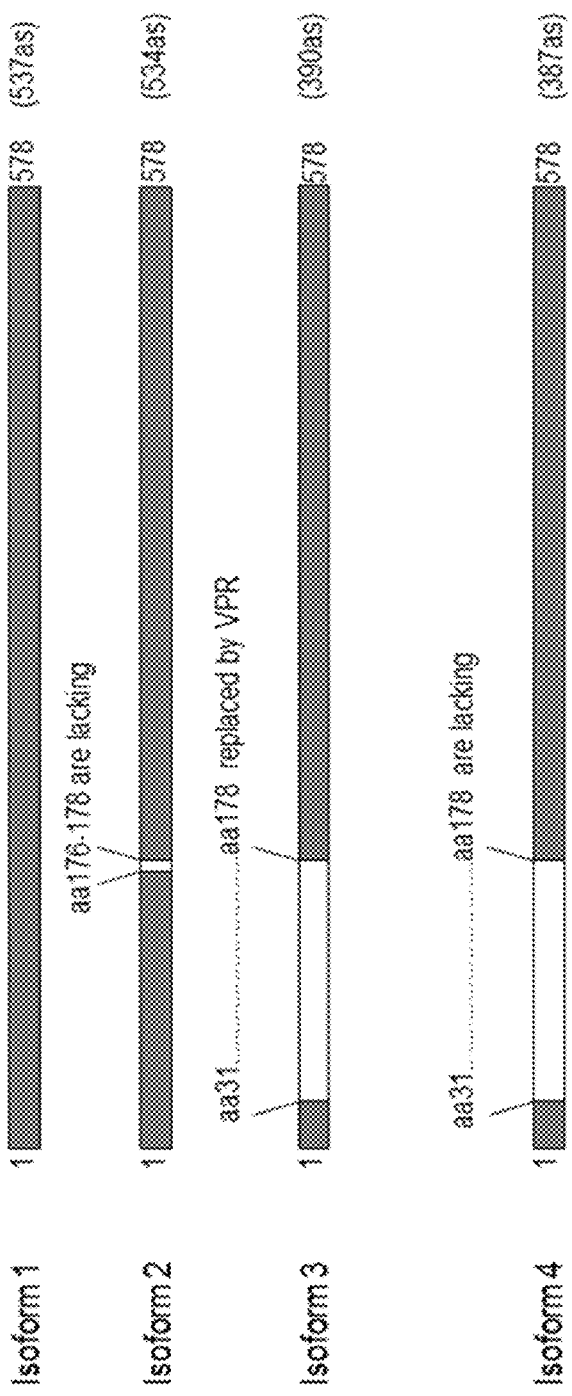
FIG. 1: Amino acid (AA) differences of the 4 isoforms of glycoprotein 2 (V, valine; P, proline; R, arginine).

For expression of the four GP2 isoforms, four plasmids coding the amino acid sequence of the GP2 isoforms NP_001007241.2 (isoform 1), NP_001493.2 (isoform 2), NP_001007242.2 (isoform 3) and NP_001007243.2 (isoform 4) (FIG. 1, tables 1-3) were employed. A thrombin cleaving site (VPRGS) and a His6-Tag were added at the C-terminal end. The obtained insert was ligated into a BamHI and EcoRI site of a pVL1393-vector resulting into 4 plasmids (pVL-GP2xtrunc-Thrombin-His) and the constructs were verified by sequencing.

For transfection, 106 Sf9 cells were disseminated in culture medium TC-100 (Biochrom, Berlin, Germany) containing 10% FCS, 6 mM glutamine, 50 µg/ml streptomycin, and 50 U/ml penicillin, and incubated in a 25 cm2 flask for at least two hours at 28° C. For transfection, two solutions were prepared containing 2.5 µg BaculoGold (Virus-DNA, BD Biosciences, San Jose, Calif.) and 2.5 µg DNA of the pVL-GP2xtrunc-Thrombin-His vectors and Polyfect transfection reagent (Qiagen, Hilden, Germany) dissolved in distilled water, respectively. Both solutions were mixed and incubated at room temperature (RT) for 20 minutes.

The Sf9 culture medium was replaced with serum-free TC-100 and the prepared transfection solution was added to the Sf9 culture and incubated overnight at 28° C., subsequently. Afterwards, the medium was exchanged for culture medium. After 5 days, supernatant containing the recombinant virus was collected and used for further infections.

For infection of Sf9 cells with the GP2-DNA containing Baculovirus, Sf9 cells were disseminated into 150 cm$^2$ flasks with a density of 2×106 cells/cm2. The supernatant of a previous infected culture was added at a ratio of 1 to 10 and cultures were incubated on a shaker (100 rpm) at 280C for 3 days. After harvesting the supernatant for purification of the secreted GP2 isoform, GP2 expression was controlled by sodium dodecyl sulphate poly-acrylamid gelelectrophoresis (SDS-PAGE) and Western blot using anti-His and anti-human GP2 antibodies as described elsewhere.

Purification of GP2 Isoforms by Ni-chelate and Ion Exchange Chromatography

Harvested supernatants were clarified by centrifugation and subjected to an ÄKTA-FPLC (GE Healthcare, Munchen, Germany) controlled Ni-chelate column (His-Trap, 1 ml, GE Healthcare) equilibrated with binding buffer (20 mM Na-phosphate, 200 mM NaCl, 50 mM imidazol, pH8.0). To remove unbound protein, the column was subsequently rinsed with 7 ml binding buffer. Bound proteins were eluted with 500 mM imidazol in a 20 mM Na-phosphate solution (pH7.5). Fractions were collected and stored with 0.01% sodium azide at 400 until further purification.

For anion exchange chromatography, a Mono Q 5/50 column (SGE Healthcare) was equilibrated with 20 mM Na-phosphate (pH7.5). After application of the GP2 containing solution, bound proteins were eluted with a 1 M NaCl gradient in a 20 mM Na-phosphate buffer (pH7.5). Glycoprotein 2 containing fractions were pooled, dialyzed against 50 mM Tris buffer (pH7.5), and stored with 0.01% sodium azide at 400 until further use.

Detection of Anti-GP2 Isoform Antibodies by ELISA

IgG and IgA against the 4 GP2 isoforms were assessed in serum samples of patients and controls by an enzyme-linked immunosorbent assay (ELISA). As solid-phase antigenic targets, these assays employ the different recombinant human GP2 isoforms expressed in *Spodoptera frugiperda* 9 cells. Briefly, GP2 isoforms at a concentration of 5 µg/ml were coated onto Maxisorb microtiter plates (Nunc, Roskilde, Denmark) in coating buffer (pH 9.5) at 4° C. After blocking at RT for one hour, serum samples diluted 1 in 100 were incubated at RT for one hour and washed. Horseradish peroxidase-conjugated anti-human IgG or IgA antibodies (Seramun GmbH, Heidesee, Germany) were added and developed with ready-to-use hydrogen peroxide/tetramethylbenzidine substrate (Seramun, Heidesee, Germany). The reaction was stopped with 0.25 mol/l sulphuric acid after 15 minutes. The optical density (OD) of the samples was read using a microplate reader (SLT, Crailsheim, Germany) at a wavelength of 450 nm/620 nm.

ELISA for the Detection of CeD-Specific Antibodies

Serum IgA and IgG antibodies to human recombinant tTG (anti-tTG) and dDG (anti-dGD) were determined by ELISA according to the instructions of the manufacturer (GA Generic Assays GmbH) [Conrad et al, 2011]. The optical density was read in a microplate reader at 450 nm and results expressed as arbitrary units (U/ml). The cut off for positivity at 10 U/ml in accordance with the recommendations of the manufacturer was used for these assays. The functional assay sensitivity [Zöphel et al., 2009] was determined at 2 U/ml and 3 U/ml for anti-tTG and anti-dGD IgA, respectively, and 3 U/ml and 2 U/ml for IgG to tTG and dGD, respectively.

Statistical Analysis

The two-tailed, non-parametric Mann-Whitney and Kruskal-Wallis tests were used to test for statistically significant differences of independent samples in 2 or more groups, respectively. The non-parametric Wilcoxon test was employed to test paired samples. P values of less than 0.05 were considered significant. Calculations were performed using Medcalc statistical software (Medcalc, Mariakerke, Belgium).

Example 1: Anti-Glycoprotein 2 Antibodies in Patients with Celiac Disease are Directed Against the Long Isoforms 1 and 2

The experiments provided herein show that in serum samples obtained from CeD patients, significantly higher levels of IgG to the isoform 1, 2, and 3 of GP2 cGP2red with those in blood donors were observed. IgG reactivity to isoform 4 was not different (p >0.05). In contrast, IgA levels to all four GP2 isoforms showed significantly higher levels in de-novo celiac disease patients than in controls. There was a significantly higher reactivity of IgG and IgA to the longer GP2 isoforms 1 and 2 of GP2 cGP2red with the shorter isoforms 3 and 4.

Subjects

Ten serum samples from patients with de-novo CeD and 50 control sera from healthy blood donors (BD) were assessed. The median age of the 40 patients with CeD (8 females) was 16 years with an interquartile range (IQR) from 6 years to 22 years. The median age of the BD (23 females, 27 males) was 24 years (IQR 18-41). Clinical diagnoses were based upon standard clinical, radiological, endoscopic and histological criteria.

Results

Figure 2:
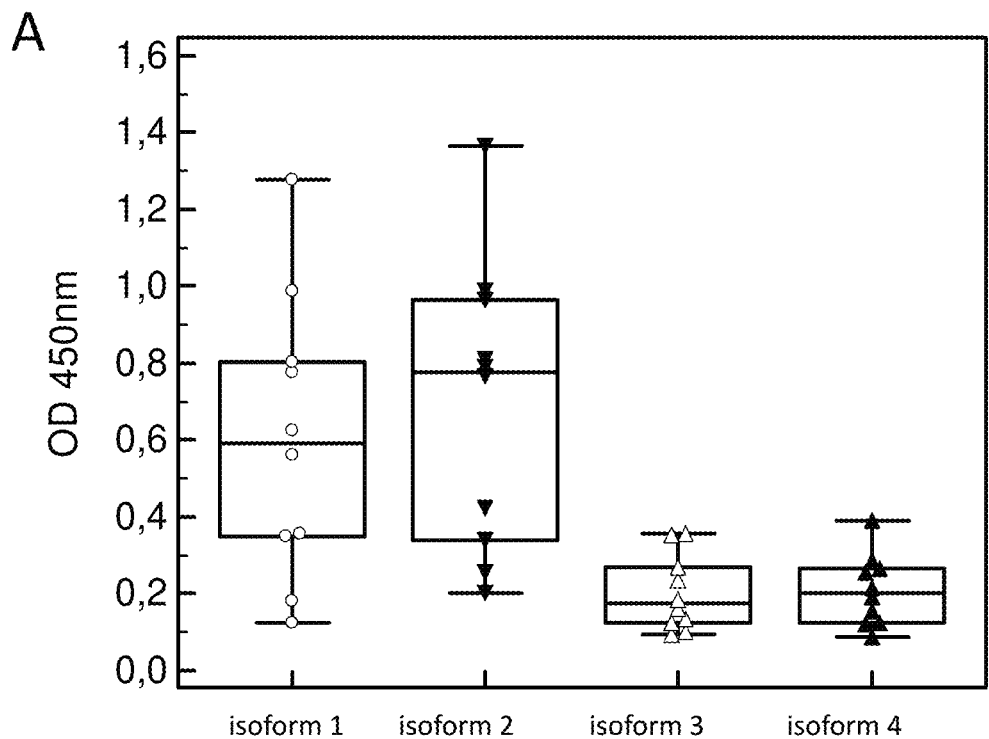
FIG. 2: Reactivity of IgG to 4 different GP2 isoforms by ELISA in 10 patients with de-novo celiac disease (A) and 50 blood donors (B). Data are displayed as optical densities (OD) in Box-and-Whisker plots with far out values, defined as values that are smaller than the lower quartile minus 3 times the interquartile range, or larger than the upper quartile plus 3 times the interquartile range, displayed as triangles.
Figure 2:
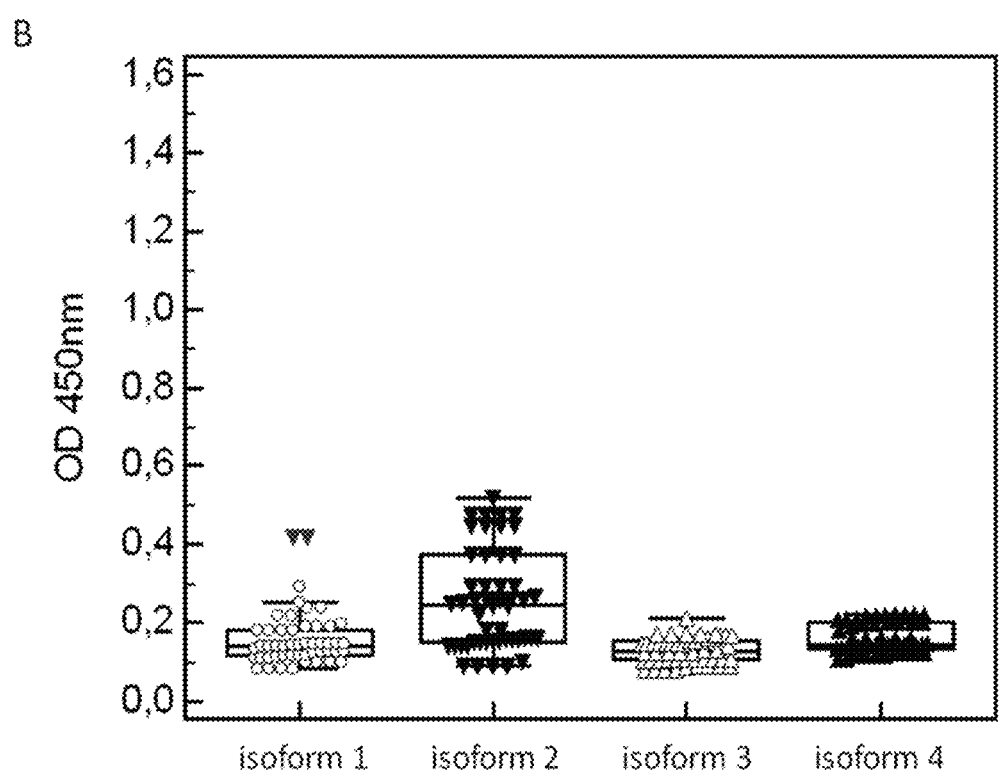
Figure 3:
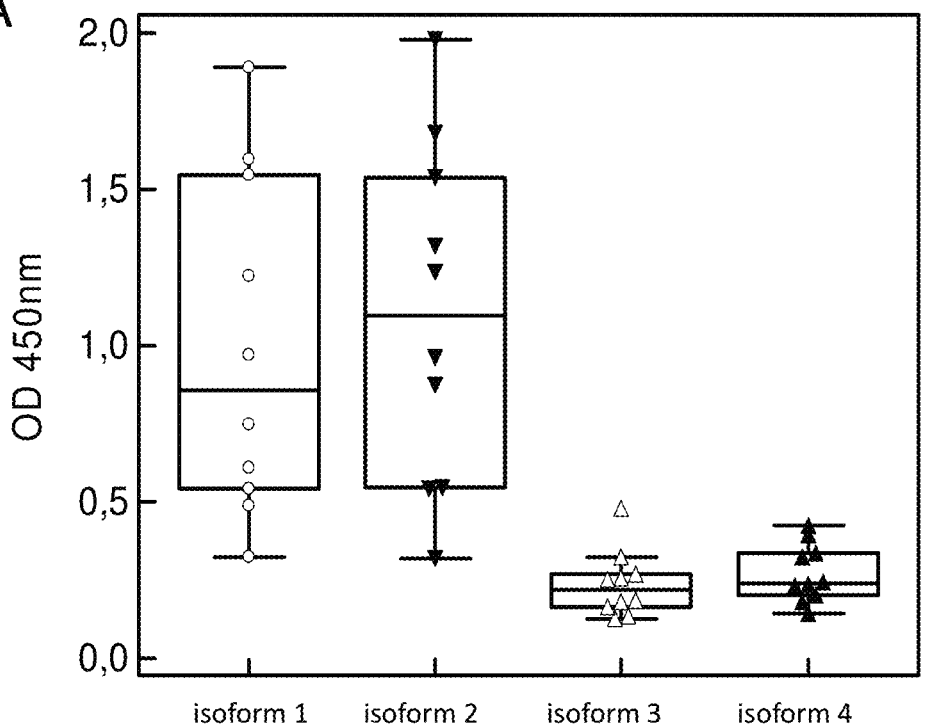
FIG. 3: Reactivity of IgA to 4 different GP2 isoforms by ELISA in 10 patients with de-novo celiac disease (A) and 50 blood donors (B). Data are displayed as optical densities (OD) in Box-and-Whisker plots with far out values, defined as values that are smaller than the lower quartile minus 3 times the interquartile range, or larger than the upper quartile plus 3 times the interquartile range, displayed as rectangles.
Figure 3:
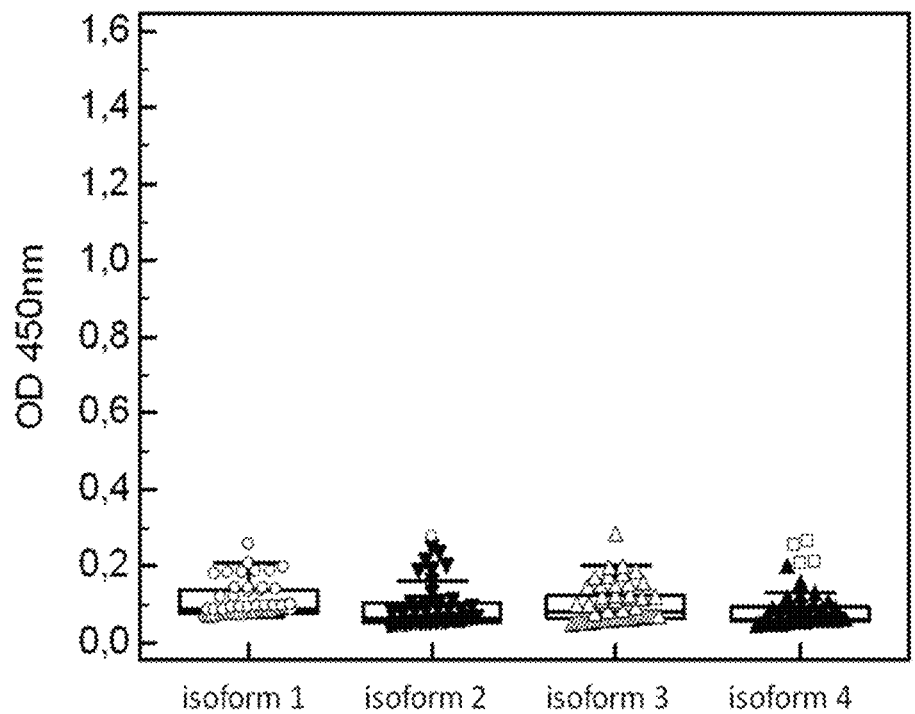
Figure 4:
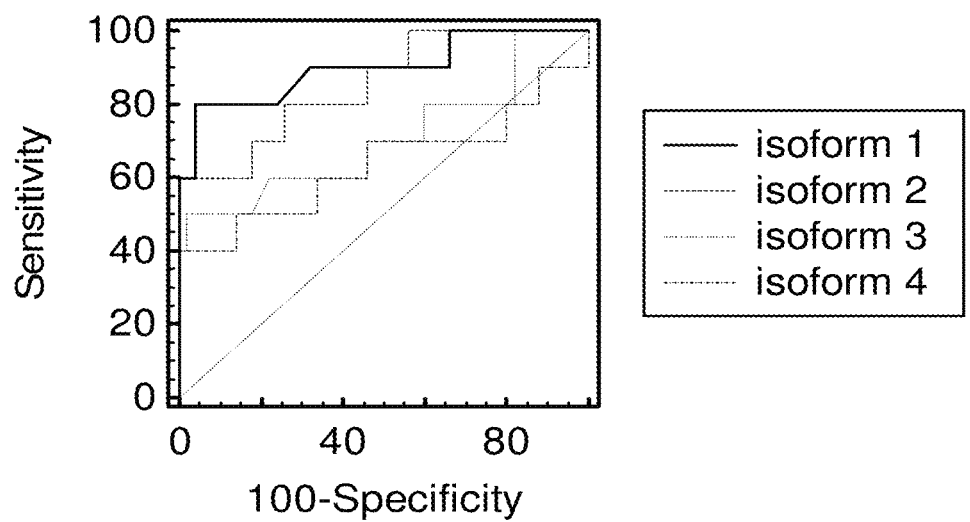
FIG. 4: Receiver operating characteristics curve analysis of IgG (A) and IgA (B) to 4 different GP2 isoforms by ELISA in 10 patients with de-novo celiac disease (A) and 50 blood donors (B)
Figure 4:
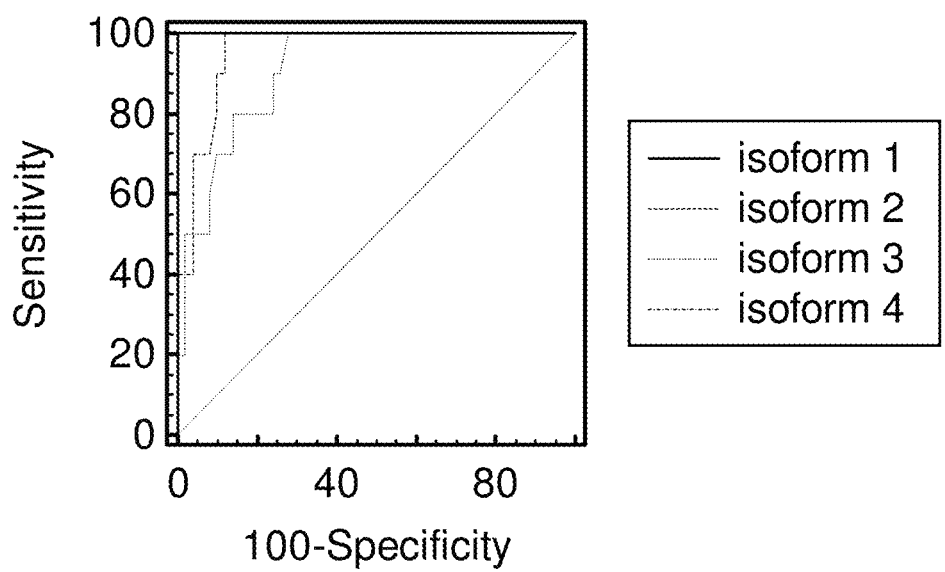

Patients with de-novo celiac disease demonstrated significantly higher levels of IgG to the isoform 1, 2, and 3 of GP2 cGP2red with those in blood donors (p=0.001, p=0.004, p=0.0388 respectively) (FIG. 2, 3). IgG reactivity to isoform 4 was not different (p>0.05). In contrast, IgA levels to all 4 GP2 isoforms showed significantly higher levels in de-novo celiac disease patients than in controls (p<0.001, respectively). There was a significantly higher reactivity of IgG and IgA to the longer GP2 isoforms 1 and 2 of GP2 cGP2red with the shorter isoforms 3 and 4 (p>0.05, respectively).

Investigating patients with de-novo celiac disease and controls, receiver operating characteristics curve analysis revealed a significantly higher area under the curve (AUC) for IgG autoantibodies to isoform 1 (0.898, 95% CI: 0.792-0.961) and 2 (0.854, 95% CI: 0.739-0.932) cGP2red with autoantibodies to isoform 4 (0.638, 95% CI: 0.505-0.758, p<0.05, respectively). There was a tendency for a higher AUC for IgG to isoform 1 and 2 in contrast to autoantibodies to isoform 3 (0.708, 95% CI: 0.576-0.818; p=0.0725, p=0.0652, respectively). IgA autoantibodies to isoform 1 (1.000, 95% CI: 0.940-1.000) and 2 (1.000, 95% CI: 0.940-1.000) demonstrated a significantly higher AUC cGP2red with autoantibodies to isoform 3 (0.912, 95% CI: 0.810-0.970, p<0.05, respectively). There was a tendency for a higher AUC for IgG to isoform 1 and 2 in contrast to autoantibodies to isoform 4 (0.957, 95% CI: 0.871-0.992; p=0.0712, p=0.0712, respectively).

In summary, autoantibodies to the longer isoforms of GP2 can be used for the diagnosis of de-novo celiac disease and are characterized by better assay performance characteristics than autoantibodies to the shorter isoforms.

Example 2: Anti-Glycoprotein 2 Antibodies in Patients with CD are Directed Against the Long Isoforms 1 and 2

The invention is also based on the finding that the GP2-isoforms as disclosed herein are surprisingly well suited for the diagnosis or therapy control of chronic inflammatory or other autoimmune diseases, especially Crohn's disease (CD) and Ulcerative colitis (UC). In particular, the novel GP2-isoforms as described herein allow a more reproducible and more accurate differentiation between CD and UC. Autoantibodies to the shorter isoforms of GP2, in particular isoform 4, can be used for the differential diagnosis of inflammatory bowel diseases and show a better differentiation of Crohn's disease and ulcerative colitis patients.

Subjects 44 patients with CD, 30 patients with UC and 21 blood donors were tested for anti-GP2 iso-types IgG and IgA. Clinical diagnoses were based upon standard clinical, radiological, endoscopic and histological criteria.

Results

Figure 5:
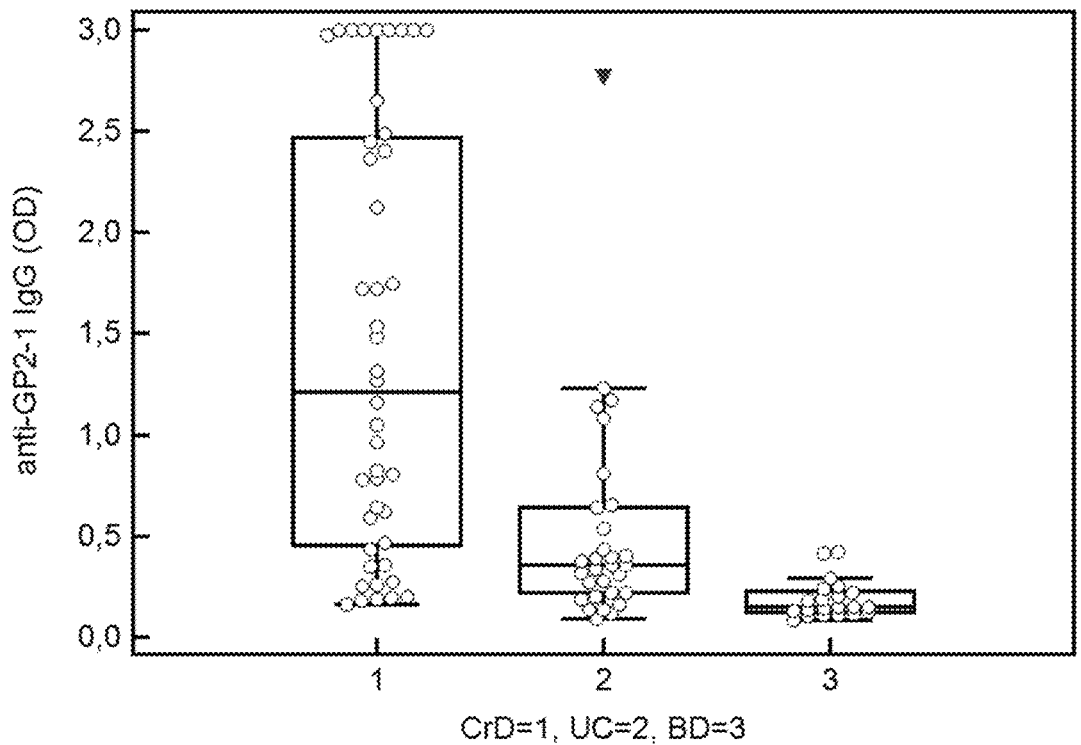
FIG. 5: Reactivity of IgG to Isoform 1 of GP2 in 44 patients with CD, 30 patients with UC and 21 blood donors. Data are displayed as optical densities (OD) in Box-and-Whisker plots with far out values, defined as values that are smaller than the lower quartile minus 3 times the interquartile range, or larger than the upper quartile plus 3 times the interquartile range, displayed as triangles.

IgG to GP2 isoform 1 demonstrated significantly different OD values in 44 patients with CD, 30 patients with UC and 21 blood donors (FIG. 5, p<0.0001). Patients with CD demonstrated elevated IgG to GP2 isoform 1 compared with those in patients with UC and blood donors (p<0.05). Furthermore, patients with UC had higher antibodies to isoform 1 than blood donors did (p<0.05).

Figure 6:
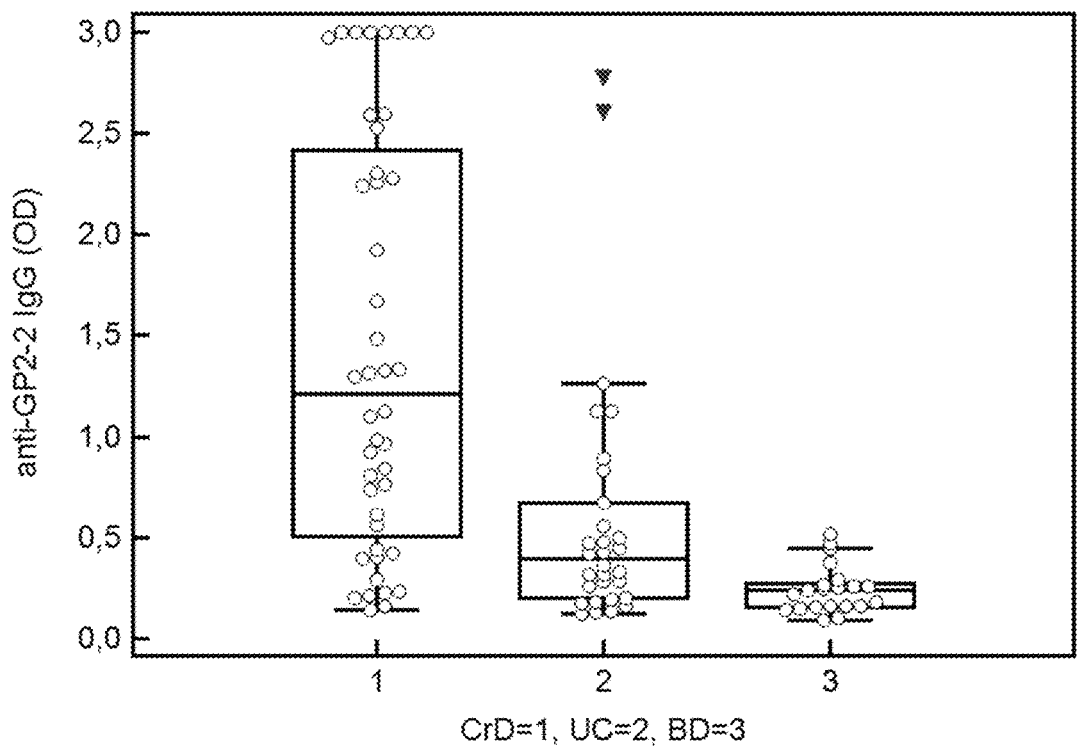
FIG. 6: Reactivity of IgG to Isoform 2 of GP2 in 44 patients with CD, 30 patients with UC and 21 blood donors. Data are displayed as optical densities (OD) in Box-and-Whisker plots with far out values, defined as values that are smaller than the lower quartile minus 3 times the interquartile range, or larger than the upper quartile plus 3 times the interquartile range, displayed as triangles.
Figure 8:
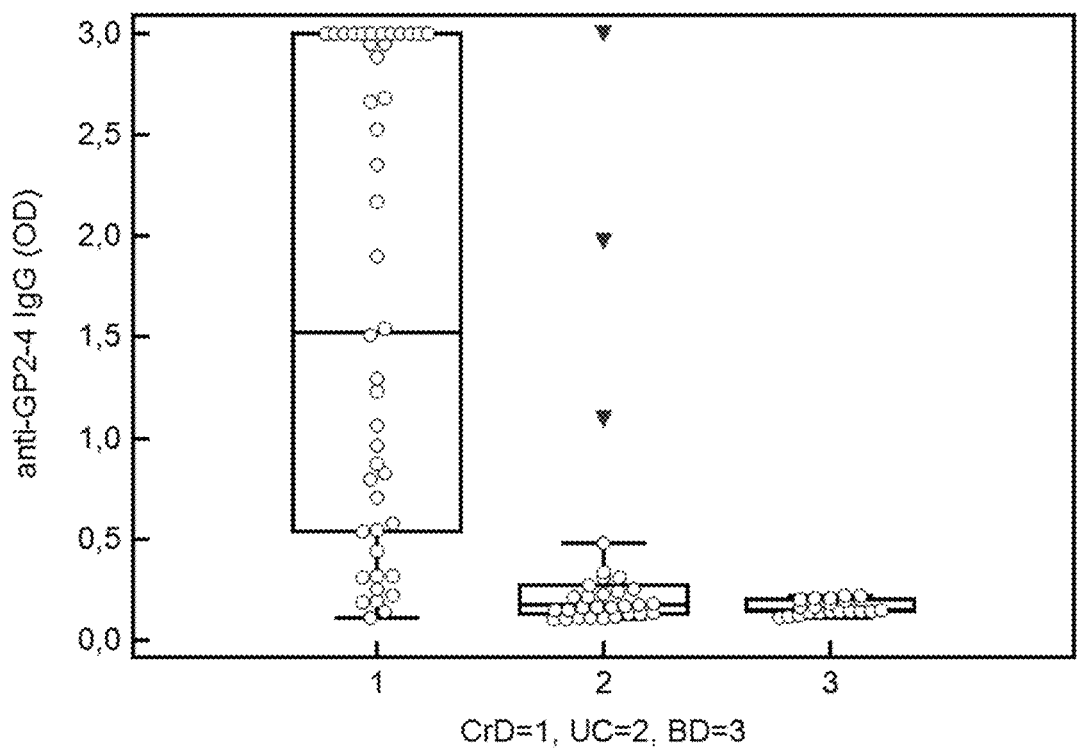
FIG. 8: Reactivity of IgG to Isoform 4 of GP2 in 44 patients with CD, 30 patients with UC and 21 blood donors. Data are displayed as optical densities (OD) in Box-and-Whisker plots with far out values, defined as values that are smaller than the lower quartile minus 3 times the interquartile range, or larger than the upper quartile plus 3 times the interquartile range, displayed as triangles.

Likewise IgG to GP2 isoforms 2 and 3 demonstrated also significantly different OD values in 44 patients with CD, 30 patients with UC and 21 blood donors (FIG. 6,7, p<0.0001). Patients with CD showed elevated IgG to GP2 isoforms 2 and 3 compared with those in patients with UC and blood donors (p<0.05, respectively). Furthermore, patients with UC had higher antibodies to isoform 2 and 3 than blood donors did (p<0.05, respectively). IgG to GP2 isoform 4 demonstrated also significantly different OD values in 44 patients with CD, 30 patients with UC and 21 blood donors (FIG. 8, p<0.0001). Patients with CD revealed elevated IgG to GP2 isoform 4 compared with those in patients with UC and blood donors (p<0.05). However, patients with UC did not have a different antibody level to isoform 4 compared with blood donors (p>0.05).

IgA to GP2 isoforms 1,3 and 4 demonstrated also significantly different OD values in 44 patients with CD, 30 patients with UC and 21 blood donors (p<0.0001). Patients with CD showed elevated IgA to GP2 isoforms 1,3 and 4 compared with those in patients with UC and blood donors (p<0.05, respectively). However, patients with UC did not have a different antibody level those 3 isoforms compared with blood donors (p>0.05).

IgA to GP2 isoform 2 demonstrated also significantly different OD values in 44 patients with CD, 30 patients with UC and 21 blood donors (p<0.0001). Patients with CD revealed elevated IgG to GP2 isoform 2 compared with those in patients with UC (p<0.05) and but not in blood donors (p>0.05).

The results show that, through a receiver operating characteristic (ROC) analysis, the novel GP2-isoforms, in particular GP2-isoform 4, enable an improved detection and/or discrimination for the serological diagnosis of Crohn's disease (CD) and Ulcerative colitis (CU).

Figure 7:
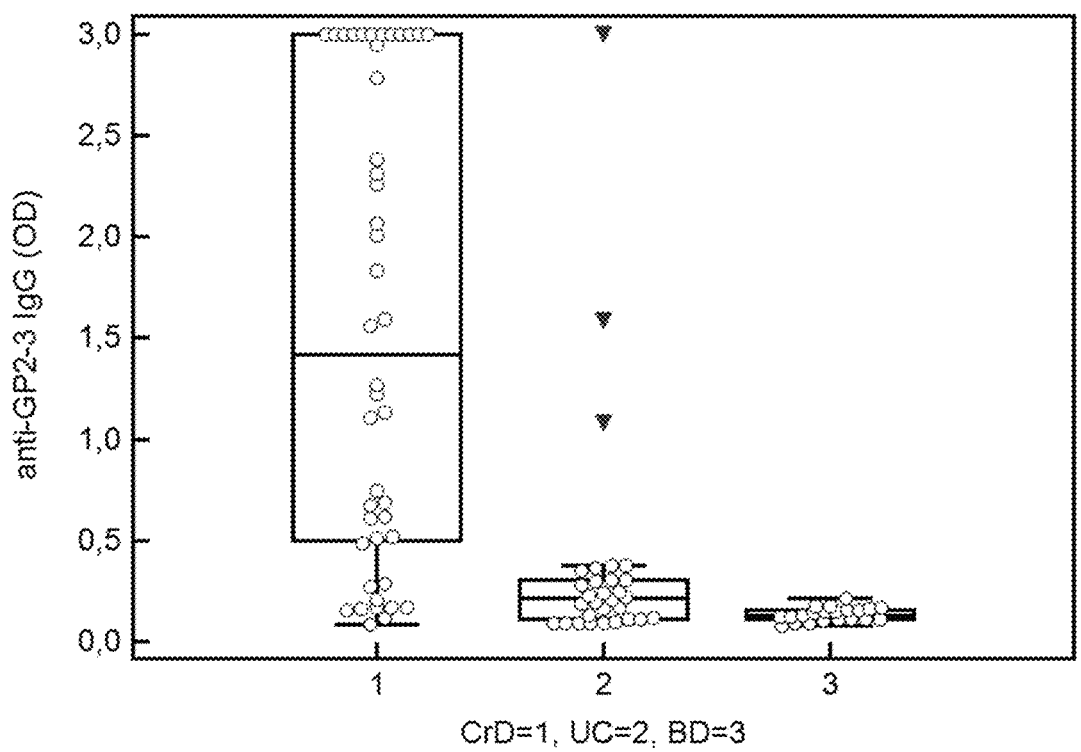
FIG. 7: Reactivity of IgG to Isoform 3 of GP2 in 44 patients with CD, 30 patients with UC and 21 blood donors. Data are displayed as optical densities (OD) in Box-and-Whisker plots with far out values, defined as values that are smaller than the lower quartile minus 3 times the interquartile range, or larger than the upper quartile plus 3 times the interquartile range, displayed as triangles.

The experiments disclosed herein demonstrate that clear differentiation between CD and UC is possible at the serological level by using the isoforms disclosed herein, preferably isoforms 3 and/or 4 of GP2 (FIGS. 7 and 8). As can be observed in these figures, the IgG autoantibodies of UC patients do not bind the isoforms 3 and 4 of GP2. Therefore, the use of isoforms 3 and 4 in the diagnostic method as described herein will enable clear differentiation between CD and UC patients.

Example 3: Mucosal Autoimmunity to Cell-Bound GP2 Isoforms is a Sensitive Marker in PSC and Associated with the Clinical Phenotype The prevalence of autoantibodies (autoAbs) to GP2-isoforms 1, 2, 3 and/or 4 (hereinafter also referred to as "aGP2$_{1-4}$") and their association with the PSC phenotype for risk prediction was examined.

GP2 isoforms were stably expressed as glycosylphosphatidylinositol-anchored molecules in the membrane of HEp-2-cells and used as autoantigenic targets in indirect immunofluorescence assay (IFA). aGP2$_{1-4}$ IgA and IgG were detected by IFA in 212 PSC patients of four European university hospitals and 145 controls comprising 95 patients with cystic fibrosis and 50 healthy subjects.

Combined aGP2$_1$ and aGP2$_4$ IgA testing with a sensitivity of 66.0% and a specificity of 97.9% resulted in the best diagnostic performance (Youden index: 0.64) regarding all aGP2 and combinations thereof, aGP2$_4$ IgA positivity was significantly associated with the presence of cirrhosis in PSC (p=0.0056). Logistic regression revealed the occurrence of aGP2$_1$ IgA (odds ratio [OR] 1.38, 95% confidence interval [CI]: 1.03-1.86) and aGP2$_4$ IgA (OR 1.52, 95% CI: 1.07-2.15) along with male gender (OR 0.51, 95% CI: 0.27-0.97) and older age (OR 1.03 95% CI: 1.01-1.05) as significant risks for the concomitant presence of cirrhosis in PSC. Autoantibodies to GP2 were significantly elevated in PSC patients. Combined aGP2$_1$ and aGP2$_4$ IgA analysis is a preferred method for sensitive PSC autoantibody testing.

Positivity for $aGP2_1$ and $aGP2_4IgA$ was shown to be associated with cirrhosis in PSC and can be used for risk stratification.

Example Introduction

Given the association of PSC with IBD, the occurrence of aGP2 IgA in severe PSC now provides evidence for the correlation of the mucosal loss of tolerance to GP2 with fibrostenotic changes as reported in IBD. Remarkably, a recent comprehensive retrospective outcome analysis of 7,121 PSC patients at 37 centers in Europe, North America, and Australia revealed that 70% of them developed IBD at some point. Conversely, PSC appeared to be underestimated around three-fold in long-term IBD and to progress in subclinical IBD patients.

In total, four human GP2 isoforms, namely GP2 isoforms, 1, 2, 3 and/or 4 ($GP2_{1-4}$) were employed and respective autoAbs detected in patients with IBD which demonstrated differing test performances by enzyme-linked immunosorbent assay (ELISA). Hence, stable HEp-2 cell-lines expressing GP2 isoforms as glycosylphosphatidylinositol (GPI)-anchored membrane molecules and one cell line with an empty vector as control were generated to elucidate the role of loss of tolerance to GP2 isoforms in PSC. Consequently, IgG and IgA $aGP2_{1-4}$ are hereby determined by indirect immunofluorescence assay (IFA) in patients with PSC and controls.

Patients

Patients with PSC were recruited from four European university hospitals specialized in autoimmune liver diseases (Table 4). All PSC patients were examined clinically and endoscopically for concomitant IBD and autoimmune hepatitis (AIH). The diagnosis of PSC and IBD was based on clinical, radiologic, endoscopic, and histologic evaluation. Patients with cystic fibrosis (CF), a multi-systemic disorder with exocrine pancreatic insufficiency and biliary cirrhosis with a different pathogenesis, were included as disease controls. Further, 50 age- and gender-matched apparently healthy subjects (HS) with no liver or intestinal pathology were recruited as controls, constituting a control population.

Generation of GP2-Expressing Cell Lines

Stable HEp-2 cell lines expressing membrane GPI-anchored GP2 isoforms were generated through transduction with lentiviruses. Briefly, coding sequences of GP2 isoforms sequences were amplified with PCR and cloned into pLVX-IRES-puro plasmids each using T4 DNA ligase (THERMOFISHER SCIENTIFIC, Waltham, USA) in accordance with the manufacturer's protocol. To confirm successful cloning, plasmids were Sanger sequenced. For transduction, lentiviruses were produced using the Lenti-X Lentiviral Expression System (CLONTECH LABORATORIES, Mountain View, USA). Thus, an 80% confluent Lenti-X 293T cell line was co-transfected with the six plasmids containing GP2 isoforms or an "empty" vector. The harvested supernatants were concentrated by centrifugation in Amicon® Ultra-15 centrifugal filter units (MERCK MILLIPORE, Darmstadt, Germany) and employed for transduction of HEp-2 cells. Selection of successfully transduced cells was performed by adding the antibiotic puromycin to cell culture. Confirmation of GP2 transduction into HEp-2 cells was done with reverse transcription quantitative polymerase chain reaction (RT qPCR). Expression of GP2 isoform proteins was confirmed by Western blotting. Membrane expression of GPI-anchored GP2 isoforms was confirmed by flow cytometry analysis.

Detection of IgG and IgA to GP2 Isoforms

IgG and IgA to GP2 isoforms were determined by IFA employing stably transduced HEp-2 cells expressing membrane GPI-anchored GP2 isoforms 1-4. Briefly, cells were fixed on glass slides and incubated with 1 in 20 diluted sera for 1 h at room temperature. HEp2-cells transduced with an empty vector were used as negative control. After washing, bound autoAbs to GP2 isoforms were revealed by incubation of polyclonal anti-human IgG or IgA antibodies conjugated to fluorescein isothiocyanate (FITC) (AGILENT, Santa Clara, USA) for 1 h at room temperature. A fluorescent microscope (Axiovert 40®, ZEISS, Göttingen, Germany) was used to read specific staining of HEp-2 cells. Brighter fluorescent staining of the cellular membrane of transduced HEp-2 cells in comparison with HEp2-cells transduced with an empty vector was scored positive.

Statistical Methods

Data were tested for normality by the Kolmogorov-Smirnov-test and non-normally distributed data were reported by median and quartile ranges. The two-tailed, Mann-Whitney and Kruskal-Wallis tests were used to test for statistically significant differences of independent samples in 2 and more groups, respectively. Prevalence comparison between groups was performed by two-tailed Fisher's exact test. Logistic regression analysis was employed to test for the influence of explanatory (independent) variables on a binomial response variable and to detect possible clinical confounders on such association (age, gender, concomitant IBD, concomitant overlap with AIH) by a backward exclusion strategy. P values<0.05 were considered as significant. MedCalc® software version 12.7.0.0 (MEDCALC, Mariakerke, Belgium) was used for performing statistical analysis.

Results

Detection of autoantibodies to GP2 isoforms by indirect immunofluorescence was carried out as described above. As a control, one cell line was transduced with an empty vector only. The presence of membrane-bound $GP2_1$ to $GP2_4$ in the respective lines and their absence in the empty vector cell line was confirmed by FACS analysis (FIG. 10). For the detection of $aGP2_1$ to $aGP2_4$ by IFA, cells of each line were fixed to conventional glass slides and used as targets for specific autoAb analysis (FIG. 11).

Occurrence of IgA and IgG to GP2 Isoforms in Patients and Controls

IgA and IgG against $GP2_{1-4}$ were assessed in 212 patients with PSC of four European hospitals and 145 gender-matched controls. Of note, the 50 HS (healthy subjects) included as controls were gender- as well as aged-matched to all PSC patients (Table 4). Patients with PSC of the Debrecen cohort were significantly younger compared to the remaining three PSC cohorts whereas the Hamburg cohort had a significantly higher median age (p<0.05, respectively).

Notably, aGP2 demonstrated significantly elevated prevalence in PSC patients compared with controls including HS and patients with CF (p<0.05, respectively) (Table 5).

Regarding IgA reactivity, aGP2$_1$ (47.2%) and aGP2$_4$ positivity (48.6%) revealed the highest frequencies in PSC patients resulting in an even significantly elevated combined positive rate of 66.0% (aGP2$_{1and/or4}$ IgA) compared with both rates of single aGP2 isoform IgA testing (p<0.0001, =0.0004, respectively). Apart from aGP2$_3$ IgA, all other aGP2 isoform IgA demonstrated significantly lower prevalences in controls. Thus, aGP2$_{1and/or4}$ IgA testing revealed the best Youden index (YI) of 0.64 being a measure of assay performance. In terms of IgG, aGP2$_1$ and aGP2$_4$ testing revealed the highest positive rates in PSC patients, too.

Association of IgA and IgG to GP2 Isoforms with PSC Phenotypes

The possible association of the presence of IgA and IgG to GP2$_{1-4}$ in PSC patients with performed liver transplantation (LTx) and concomitant occurrence of autoimmune hepatitis, cirrhosis, cholangiocarcinoma, CD, UC, IBD (CD or UC) was investigated by Fisher's exact test (Table 6). Further, established associations were investigated by logistic regression analysis to analyze the influence of confounding factors.

A significantly positive association of aGP2 isoform IgA and IgG positivity in PSC was established for the concomitant occurrence of cirrhosis. Thus, aGP2$_1$ and aGP2$_4$ IgA as well as aGP2$_2$ and aGP2$_4$ IgG were more prevalent in PSC patients with cirrhosis than in those without (p<0.05, respectively). Similar positive associations could be found in the larger co-horts from London and Debrecen, too. Logistic regression analysis for the risk analysis of the occurrence of cirrhosis in all 212 PSC patients confirmed aGP2$_1$ and aGP2$_4$ IgA as independent predictors in older male PSC patients (Table 7).

A significantly positive association of aGP2$_3$ IgG in PSC was determined for the concomitant occurrence of cholangiocarcinoma. Regarding the single hospital cohorts, only the London cohort contained just 5 PSC patients with cholangiocarcinoma. In this cohort, an association of aGP2$_3$ IgG with cholangiocarcinoma was revealed (4/26 vs. 1/57, p=0.0316) and confirmed by the total PSC cohort (4/27 vs. 1/109, p<0.0001) (Table 6). Further, aGP2$_3$ IgG was determined as a significant predictor for the occurrence of cholangiocarcinoma in PSC patients by logistic regression analysis (p=0.0012) (Table 7). Of note, all 5 PSC patients with cholangiocarcinoma demonstrated positive aGP2$_1$ and/or aGP2$_4$ IgA.

Discussion

Since four GP2 isoforms were discovered and specific IgG and IgA against them were described in patients with IBD, the frequency of IgG and IgA to GP2 isoforms in PSC and their possible relation to the PSC phenotype as stratification factor in PSC was investigated. It was revealed that both IgA as well as IgG against multiple GP2 isoforms in PSC patients. In terms of discrimination of PSC from controls, aGP2$_1$ IgA (47.2%) and aGP2$_4$ IgA-positives (48.6%) revealed the highest frequencies amongst all aGP2. Interestingly, combination of both led to a significantly elevated sensitivity of 66.0%. Thus, combined testing of both aGP2$_1$ and aGP2$_4$ IgA appears more sensitive than the determination of IgA to just one GP2 isoform. Combined aGP2$_1$ and aGP2$_4$ IgA testing demonstrated the best diagnostic performance for PSC by a YI of 0.64 regarding the analysis of all aGP2 and combinations thereof.

As GP2$_1$ and GP2$_4$ represent long (537 amino acids) and short GP2 isoforms (387 amino acids), respectively, they could bear differing epitopes. Remarkably, GP2$_2$ and GP2$_3$ which differ from GP2$_1$ and GP2$_4$ in just three amino acids (valine-proline-arginine), respectively, demonstrated IgA binding but at reduced levels in PSC. This adds support to the notion that GP2 isoforms bear different autoantigenic epitopes, all of which should be contained in GP2-antigenic preparations in aGP2 immunoassays for proper and accurate autoAb testing.

IgG and in particular IgA against GP2 isoforms revealed different associations with the PSC phenotype. In fact, aGP2$_1$ and aGP2$_4$ IgA were demonstrated as positive predictors of cirrhosis in older males with PSC.

There is clearly a need for risk stratification in PSC and aGP2 IgA could be of prognostic value like autoAbs to gp210 do in primary biliary cholangitis. Given a potential ascending pathophysiology of PSC, aGP2 in general and in particular aGP2$_{1/4}$ IgA (i.e., IgA autoantibodies that bind GP2 isoforms 1 and/or 4") could be a stage-defining biomarker. IgG autoantibodies that bind GP2 isoform 3 (aGP2$_3$ IgG) were determined as the sole predictor for the occurrence of cholangiocarcinoma in PSC patients.

Example 4: Antibodies Against Glycoprotein 2 are Risk Factors of Severe Clinical Phenotype, Poor Outcome and Cholangiocarcinoma in Primary Sclerosing Cholangitis This example assesses the value of anti-GP2 IgA as predictive factors of progressive disease course and poor outcome in a large cohort of PSC patients.

338 patients with PSC [age range 17-73, 65% male, 26% cirrhotic, 3.8% developed CCA during follow-up] were prospectively evaluated. Anti-GP2 IgA (isoforms 1 and 4) were detected by ELISAs (GA Generic Assays, Germany). Poor disease outcome was defined as liver transplantation and/or liver-related death during a median follow-up of 14 months. IgA autoantibodies that bind GP2 isoform 1 (aGP2, IgA) occurred in 79 (23%) and aGP2$_4$ IgA in 58 (17%) patients whereas 103 (30%) patients had at least one positive aGP2 IgA. Anti-GP2$_1$, and anti-GP2$_4$, were associated with poor liver function. Cirrhosis was associated with aGP2$_4$ IgA (p=0.003). CCA occurred more often in patients with aGP2$_1$ IgA (p=0.04). Significant associations between aGP2$_1$ IgA, aGP2$_4$ IgA, and poor outcome were found (Chi$^2$=11.2, HR=2.1, 95% CI=1.4-4.2, p=0.0008; Chi$^2$=7.8, HR=2.4, 95% CI=1.3-4.5, p=0.005, respectively). Cox proportional-hazards regression indicated anti-GP2, IgA and lower albumin level as independent variables of poor outcome (p<0.0001), whereas anti-GP2$_4$ IgA was an independent risk factor of CCA (p=0.0019).

Anti-GP2 IgA identified a subgroup of PSC patients at increased risk of liver dysfunction, poor outcome, and biliary cancer. Anti-GP2 IgA may predispose to more aggressive course of the disease and may be of clinical value for risk stratification in PSC.

Abbreviations

BD, blood donor; CeD, celiac disease; CI, confidence interval; CD or CrD, Crohn's disease; CV, coefficient of variation; ELISA, enzyme-linked immunosorbent assay; GFD, gluten-free diet; GP2, Glycoprotein 2; IBD, inflammatory bowel disease; IQR, interquartile range; M cell, microfold or membranous cell; PAB, pancreatic autoantibody; PSC, primary sclerosing cholangitis; rho, Spearman's rank coefficient of correlation; RT, room temperature, UC, Ulcerative colitis.

TABLE 4

Demographic and clinical data of patients and controls.

| | n | age (IQR) | f (%) | IBD (%) | CD (%) | UC (%) | AIH (%) | cirrhosis (%) | CCa (%) | LTx (%) |
|---|---|---|---|---|---|---|---|---|---|---|
| PSC | 212 | 43.0 (23.3) | 70 (33.0) | 136 (64.2) | 17 (8.0) | 119 (56.1) | 20 (9.4) | 86 (31.6) | 5* (3.7) | 81 (38.2) |
| Berlin | 23 | 52.5 (17.5) | 6 (26.1) | 19 (82.6) | 2 (8.7) | 17 (73.9) | 1 (4.3) | 19 (82.6) | 0 | 19 (82.6) |
| Hamburg | 30 | 50.0 (17.3) | 18 (60.0) | 15 (50.0) | 4 (13.3) | 11 (36.7) | 5 (16.7) | 3 (10.0) | 0 | 0 |
| London | 83 | 46.3 (18.7) | 23 (27.7) | 53 (63.9) | 1 (1.2) | 52 (62.7) | 5 (6.0) | 49 (59.0) | 5 (6.0) | 57 (68.8) |
| Debrecen | 76 | 34.1 (21.6) | 23 (30.3) | 49 (64.5) | 10 (13.2) | 39 (51.3) | 9 (11.8) | 15 (19.7) | 0 | 6 (7.9) |
| controls | 145 | 26.9 (22.1) | 63 (43.4) | 0 | 0 | 0 | 0 | 0 | 0 | 0 |
| CF | 95 | 15.6 (20.9) | 44 (46.3) | 0 | 0 | 0 | 0 | 0 | 0 | 0 |
| HS | 50 | 36.0 (18.0) | 19 (38.0) | 0 | 0 | 0 | 0 | 0 | 0 | 0 |

AIH, autoimmune hepatitis; CCa, cholangiocarcinoma; CD, Crohn's disease; CF, cystic fibrosis; f, females; HS, healthy subjects; IQR, interquartile range; LTx, liver transplantation; n, number; PSC, primary sclerosing cholangitis; UC ulcerative colitis.
*related to 136 patients with PSC.

TABLE 5

Frequency of IgA and IgG against GP2 isoforms 1 ($aGP2_1$) to 4 ($aGP2_4$) detected by indirect immunofluorescence assay on stabile isoform-transduced HEp2 cells in 212 patients with primary sclerosing cholangitis (PSC) from different hospitals and 145 controls.

| | n | $aGP2_1$ IgA (%) | $aGP2_1$ IgG (%) | $aGP2_2$ IgA (%) | $aGP2_2$ IgG (%) | $aGP2_3$ IgA (%) | $aGP2_3$ IgG (%) | $aGP2_4$ IgA (%) | $aGP2_4$ IgG (%) | $aGP2_{1/2/3/4}$ IgA (%) | $aGP2_{1/2/3/4}$ IgG (%) | $aGP2_{1/4}$ IgA and/or IgG (%) | $aGP2_{1/4}$ IgA (%) |
|---|---|---|---|---|---|---|---|---|---|---|---|---|---|
| PSC | 212 | 100 (47.2)** | 92 (43.4)** | 21 (9.9)* | 40 (18.9)* | 10 (4.7) | 31 (14.6) | 103 (48.6)** | 81 (38.2)** | 140 (66.0)** | 119 (56.1)** | 154 (72.6)** | 140 (66.0)** |
| Berlin | 23 | 6 (26.1)** | 7 (30.4)* | 0 | 0 | 0 | 0 | 3 (13.0)* | 2 (8.7) | 8 (34.8)** | 8 (34.8) | 10 (43.5) | 8 (34.8)** |
| Hamburg | 30 | 11 (36.7)** | 12 (40.0)* | 5 (16.7)* | 1 (3.3) | 1 (3.3) | 1 (3.3) | 9 (30.0)** | 8 (26.7)* | 16 (53.3)** | 16 (53.3)** | 17 (56.7)** | 16 (53.3)** |
| London | 83 | 42 (50.6)** | 39 (47.0)** | 2 (2.4) | 28 (33.7)** | 4 (4.8) | 26 (31.3)** | 52 (62.7)** | 40 (48.2)** | 59 (71.1)** | 50 (60.2)** | 68 (81.9)** | 59 (71.1)** |
| Debrecen | 76 | 41 (53.9)** | 34 (44.7)** | 14 (18.4)** | 11 (14.5) | 5 (6.6) | 4 (5.3) | 39 (51.3)** | 31 (40.8)** | 57 (75.0)** | 45 (59.2)** | 59 (77.6)** | 57 (75.0)** |
| Controls | 145 | 2 (1.4) | 11 (7.6) | 1 (0.7) | 12 (8.3) | 4 (2.8) | 20 (13.8) | 1 (0.7) | 11 (7.6) | 6 (4.1) | 33 (22.8) | 34 (23.4) | 3 (2.1) |
| CF | 95 | 1 (1.1) | 8 (8.4) | 1 (1.1) | 9 (9.5) | 4 (4.2) | 18 (18.9)§ | 1 (1.1) | 9 (9.5) | 5 (5.3) | 26 (27.4)§ | 26 (27.4) | 2 (2.1) |
| HS | 50 | 1 (2.0) | 3 (6.0) | 0 | 3 (6.0) | 0 | 2 (4.0) | 0 | 2 (4.0) | 1 (2.0) | 7 (14.0) | 8 (16.0) | 1 (2.0) |
| YI (PSC vs. controls) | | 0.46 | 0.36 | 0.09 | 0.11 | 0.02 | 0.00 | 0.48 | 0.31 | 0.62 | 0.33 | 0.49 | 0.64 |

CF, cystic fibrosis, f, females; HS, healthy subjects; IQR, interquartile range; n, number; YI, Youden index (specificity + sensitivity − 1).
Comparison of the prevalence of positive GP2Ab in patients with primary sclerosing cholangitis with controls (n = 145): *p < 0.05, **p < 0.0001.
Comparison of the prevalence of positive GP2Ab in patients with cystic fibrosis with healthy subjects (n = 50): §p < 0.05.

TABLE 6

Positive and negative (italic) significant associations of IgA and IgG against GP2 isoforms 1 ($aGP2_1$) to 4 ($aGP2_4$) with the clinical phenotype in 212 patients with primary sclerosing cholangitis (PSC).

| | n | IBD | CD | UC | AIH | cirrhosis | CCa | LTx |
|---|---|---|---|---|---|---|---|---|
| PSC | 212 | | $aGP2_{1/4}$ IgA<br>p = 0.01386<br>$aGP2_{1/2/3/4}$ IgA<br>p =0.0076 | | | $aGP2_4$ IgA<br>p = 0.0051<br>$aGP2_{1/4}$ IgA<br>p = 0.0056<br>$aGP2_2$ IgG<br>p = 0.0199<br>$aGP2_4$ IgG<br>p = 0.0447 | $aGP2_3$ IgG<br>p < 0.0001 | $aGP2_2$ IgA<br>p = 0.0006 |
| Berlin | 23 | | | | | | | |
| Hamburg | 30 | | | $aGP2_2$ IgA<br>p = 0.0472 | | | | |
| London | 83 | aGP23 IgG<br>p = 0.0288 | | | | $aGP2_4$ IgA<br>p = 0.0055<br>$aGP2_{1/2/3/4}$ IgA<br>p = 0.0144 | $aGP2_3$ IgG<br>p = 0.0316 | |
| Debrecen | 76 | | | | | $aGP2_2$ IgA<br>p = 0.0261<br>$aGP2_2$ IgG<br>p = 0.0349 | | |

AIH, autoimmune hepatitis; CCa, cholangiocarcinoma; CD, Crohn's disease; LTx, liver transplantation; n, number; PSC, primary sclerosing cholangitis; UC ulcerative colitis.

TABLE 7

Logistic regression analysis of independent variables for the risk prediction of liver transplantation (LTx) and the occurrence of cirrhosis and cholangiocarcinoma (CCa) and in 212 patients with primary sclerosing cholangitis (PSC). The presence of IgA and IgG to GP2 isoforms 1 ($aGP2_1$) to 4 ($aGP2_4$) and the concomitant occurrence of inflammatory bowel disease, Crohn's disease, ulcerative colitis (UC), and autoimmune hepatitis overlap as well as age and gender were used as possible predictive independent variables for the logistic regression analysis.

| Dependent variable | Independent variable | Coefficient | SE | OR | 95% CI | p |
|---|---|---|---|---|---|---|
| cirrhosis | $aGP2_1$ IgA | 0.3243 | 0.1514 | 1.3831 | 1.0279-1.8609 | 0.0322 |
| | $aGP2_4$ IgA | 0.1729 | 0.1771 | 1.5178 | 1.0727-2.1478 | 0.0185 |
| | age | 0.0273 | 0.0100 | 1.0277 | 1.0077-1.0480 | 0.0063 |
| | gender | −0.6693 | 0.3235 | 0.5121 | 0.2716-0.9654 | 0.0385 |
| LTx | $aGP2_2$ IgA | −3.02104 | 1.27092 | 0.0488 | 0.0040-0.5886 | 0.0175 |
| | cirrhosis | 3.70772 | 0.49727 | 40.7608 | 15.3800-108.0262 | <0.0001 |
| | AIH overlap | −2.63423 | 1.00286 | 0.0718 | 0.0101-0.5124 | 0.0086 |
| | UC | 1.82313 | 0.49012 | 6.1912 | 2.3691-16.1799 | 0.0002 |
| CCa | $aGP2_3$ IgG | 3.05739 | 0.94088 | 21.2721 | 3.3645-134.4943 | 0.0012 |

CI, confidence interval, OR, odds ratio; SE, standard error.

LITERATURE

1. Ronzio R A, Kronquist K E, Lewis D S, MacDonald R J, Mohrlok S H, O'Donnell J J, Jr.: Glycoprotein synthesis in the adult rat pancreas. IV. Subcellular distribution of membrane glycoproteins. *Biochim Biophys Acta* 1978, 508:65-84.
2. Roggenbuck D, Hausdorf G, Martinez-Gamboa L, Reinhold D, Buttner T, Jungblut P R, Porstmann T, Laass M W, Henker J, Buning C et al.: Identification of GP2, the major zymogen granule membrane glycoprotein, as the autoantigen of pancreatic antibodies in Crohn's disease. *Gut* 2009, 58:1620-1628.
3. Komorowski L, Teegen B, Probst C, Aulinger-Stocker K, Sina C, Fellermann K, Stocker W: Autoantibodies against exocrine pancreas in Crohn's disease are directed against two antigens: The glycoproteins CUZD1 and GP2. *J Crohns Colitis* 2012,pii: S1873-9946(12)00433-3. doi: 10.1016/j.crohns.2012.10.011. [Epub ahead of print].
4. Hase K, Kawano K, Nochi T, Pontes G S, Fukuda S, Ebisawa M, Kadokura K, Tobe T, Fujimura Y, Kawano S et al.: Uptake through glycoprotein 2 of FimH(+) bacteria by M cells initiates mucosal immune response. *Nature* 2009, 462:226-230.
5. Terahara K, Yoshida M, Igarashi O, Nochi T, Pontes G S, Hase K, Ohno H, Kurokawa S, Mejima M, Takayama N et al.: Comprehensive gene expression profiling of Peyer's patch M cells, villous M-like cells, and intestinal epithelial cells. *J Immunol* 2008, 180:7840-7846.
6. Werner L, Paclik D, Fritz C, Reinhold D, Roggenbuck D, Sturm A: Identification of pancreatic Glycoprotein 2 as an endogenous immunomodulator of innate and adaptive immune responses. *J Immunol* 2012, 189:2774-2783.
7. Holzl M A, Hofer J, Kovarik J J, Roggenbuck D, Reinhold D, Goihl A, Gartner M, Steinberger P, Zlabinger G J: The zymogen granule protein 2 (GP2) binds to scavenger receptor expressed on endothelial cells I (SREC-I). *Cell Immunol* 2011, 267:88-93.
8. Baumgart M, Dogan B, Rishniw M, Weitzman G, Bosworth B, Yantiss R, Orsi R H, Wiedmann M, McDonough P, Kim S G et al.: Culture independent analysis of ileal mucosa reveals a selective increase in invasive Escherichia coli of novel phylogeny relative to depletion of Clostridiales in Crohn's disease involving the ileum. *ISME J* 2007, 1:403-418.
9. Sollid L M: Coeliac disease: dissecting a complex inflammatory disorder. *Nat Rev Immunol* 2002, 2:647-655.
10. Tibble J, Sigthorsson G, Foster R, Sherwood R, Fagerhol M, Bjarnason I: Faecal calprotectin and faecal occult blood tests in the diagnosis of colorectal carcinoma and adenoma. *Gut* 2001, 49 2001, 49:402-408.
11. de K S, Keszthelyi D, Masclee A A: Leaky gut and diabetes mellitus: what is the link? *Obes Rev* 2011, 12:449-458.
12. Bossuyt X: Serologic markers in inflammatory bowel disease. *Clin Chem* 2006, 52:171-181.
13. Bonifacio E, Lampasona V, Genovese S, Ferrari M, Bosi E: Identification of protein tyrosine phosphatase-like IA2 (islet cell antigen 512) as the insulin-dependent diabetes-related 37/40K autoantigen and a target of islet-cell antibodies. *J Immunol* 1995, 155:5419-5426.
14. Baekkeskov S, Kanaani J, Jaume J C, Kash S: Does GAD have a unique role in triggering IDDM? *J Autoimmun* 2000, 15:279-286.
15. Conrad K, Schmechta H, Klafki A, Lobeck G, Uhlig H H, Gerdi S, Henker J: Serological differentiation of inflammatory bowel diseases. *Eur J Gastroenterol Hepatol* 2002, 14:129-135.
16. Bogdanos D P, Roggenbuck D, Reinhold D, Wex T, Pavlidis P, von Arnim U, Malfertheiner P, Forbes A, Conrad C, Laass M: Pancreatic-specific autoantibodies to glycoprotein 2 mirror disease location and behaviour in younger patients with Crohn's disease. *BMC Gastroenterol* 2012, 12:102.
17. Rieder F, Franke A, Dirmeier A, Lopez R, Lang S, Roggenbuck D, Rogler G, Klebl F: Mo1247 Serologic Anti-GP2 Antibodies Are Associated With Strictures and Need for Surgical Resection in Crohn's Disease. *Gastroenterology* 2013, 144:-S617.
18. Roggenbuck D, Reinhold D, Werner L, Schierack P, Bogdanos D P, Conrad K: Glycoprotein 2 antibodies in Crohn's disease. *Adv Clin Chem* 2013, 60:187-208.
19. Roggenbuck D, Reinhold D, Wex T, Goihl A, von Arnim U, Malfertheiner P, Buttner T, Porstmann T, Porstmann S, Liedvogel B et al.: Autoantibodies to GP2, the major zymogen granule membrane glycoprotein, are new markers in Crohn's disease. *Clin Chim Acta* 2011, 412:718-724.
20. Bogdanos D P, Rigopoulou E I, Smyk D S, Roggenbuck D, Reinhold D, Forbes A, Laass M W, Conrad K: Diagnostic value, clinical utility and pathogenic significance of reactivity to the molecular targets of Crohn's disease specific-pancreatic autoantibodies. *Autoimmun Rev* 2011, 11:143-148.
21. Op De B K, Vermeire S, Rutgeerts P, Bossuyt X: Antibodies to GP2, the major zymogen granule membrane glycoprotein, in inflammatory bowel diseases. *Gut* 2010.
22. Pavlidis P, Romanidou O, Roggenbuck D, Mytilinaiou M, Al-Sulttan F, Liaskos C, Smyk D S, Koutsoumpas A, Rigopoulou E, Conrad K et al.: Ileal inflammation may trigger the development of GP2-specific pancreatic autoantibodies in patients with crohn's disease. *Clin Dev Immunol* 2012, 2012:640835.
23. Somma V, Ababneh H, Ababneh A, Gatti S, Romagnoli V, Bendia E, Conrad K, Bogdanos D P, Roggenbuck D, Ciarrocchi G: The Novel Crohn's Disease Marker Anti-GP2 Antibody Is Associated with Ileocolonic Location of Disease. *Gastroenterol Res Pract* 2013, 2013:683824.
24. Roggenbuck D, Reinhold D, Schierack P, Bogdanos D P, Conrad K, Laass M W: Crohn's disease specific pancreatic antibodies: clinical and pathophysiological challenges. *Clin Chem Lab Med* 2013,1-12.
25. Bonaci-Nikolic B, Spuran M, Andrejevic S, Nikolic M: Autoantibodies to GP2, the major zymogen granule membrane glycoprotein, in patients with gluten-sensitive enteropathy: A possible serological trap. *Clin Chim Acta* 2012, 413:822-823.
26. Ludvigsson J F, Leffler D A, Bai J C, Biagi F, Fasano A, Green P H R, Hadjivassiliou M, Kaukinen K, Kelly C P, Leonard J N et al: The Oslo definitions for coeliac disease and related terms [abstract].2012, 1
27. Soderholm J D, Peterson K H, Olaison G, Franzen L E, Westrom B, Magnusson K E, Sjodahl R: Epithelial permeability to proteins in the noninflamed ileum of Crohn's disease? *Gastroenterology* 1999, 117:65-72.
28. Bjarnason I: Intestinal permeability. *Gut* 1994, 35:S18-S22.
29. Baumgart D C, Carding S R: Inflammatory bowel disease: cause and Immunobiology. *Lancet* 2007, 369: 1627-1640.
30. Rieder F, Lawrance I C, Leite A, Sans M: Predictors of fibrostenotic Crohn's disease. *Inflamm Bowel Dis* 2011, 17:2000-2007.
31. Bardella M T, Elli L, De M S, Floriani I, Torri V, Piodi L: Autoimmune disorders in patients affected by celiac sprue and inflammatory bowel disease. *Ann Med* 2009, 41:139-143.
32. Fasano A: Leaky gut and autoimmune diseases. *Clin Rev Allergy Immunol* 2012, 42:71-78.
33. Fukuoka S: Molecular cloning and sequences of cDNAs encoding alpha (large) and beta (small) isoforms of human pancreatic zymogen granule membrane-associated protein GP2. *Biochim Biophys Acta* 2000, 1491:376-380.
34. Conrad K, Roggenbuck D, Ittenson A, Reinhold D, Buettner T, Laass M W: A new dot immunoassay for simultaneous detection of celiac specific antibodies and IgA-deficiency. *Clin Chem Lab Med* 2011, 50:337-343.
35. Zöphel K, Wunderlich G, Kotzerke J, von Landenberg P, Roggenbuck D: M22 based (manual) ELISA for TSH-receptor antibody (TRAb) measurement is more sensitive than 2nd generation TRAb assays. *Clin Chim Acta* 2009, 403:266.

What I claim is:

1. An in vitro method for diagnosing and treating an autoimmune disorder, where the autoimmune disorder is primary sclerosing cholangitis (PSC), by detection of autoantibodies from a sample that bind to one or more isoforms of Glycoprotein 2 (GP2), comprising:
   providing the sample of a subject exhibiting symptoms of and/or suspected of having said disorder,
   providing two or more isoforms of GP2 comprising at least isoform 1 and/or 2 of GP2 and isoform 3 and/or 4 of GP2,
   contacting said sample with said isoforms of GP2,
   measuring an amount of the IgG and/or the IgA autoantibodies that bind said isoform 1 and/or 2 of GP2 and isoform 3 and/or 4 of GP2 in the sample,
   comparing the amount of the IgG and/or the IgA autoantibodies that have bound GP2 isoforms 1 and/or 2 and isoform 3 and/or 4 to a reference value of the amount of IgG and/or IgA autoantibodies that bind GP2 isoforms 1 and/or 2 and isoform 3 and/or 4 in a healthy control population,
   diagnosing said subject with PSC when the amount of the IgG and/or the IgA autoantibodies that have bound GP2 isoforms 1 and/or 2 and isoform 3 and/or 4 is higher than said reference value, and
   treating the subject with an anti-PSC treatment when the subject is diagnosed with PSC.

2. The method according to claim 1, wherein isoform 1 of GP2 has a protein sequence consisting of SEQ ID NO 1, isoform 2 of GP2 has a protein sequence consisting of SEQ ID NO 2, isoform 3 of GP2 has a protein sequence consisting of SEQ ID NO 3, and isoform 4 of GP2 has a protein sequence consisting of SEQ ID NO 4.

3. The method according to claim 1, wherein said method comprises using a kit for detecting autoantibodies from the sample that bind to one or more isoforms of Glycoprotein 2 (GP2), wherein the kit comprises at least one protein with an amino acid sequence consisting of SEQ ID NO 1 or 2, and at least one protein with an amino acid sequence consisting of SEQ ID NO 3 or 4.

4. The method according to claim 3, wherein the kit comprises isoforms 1, 2, 3 and 4 of Glycoprotein 2 (GP2).

5. The method according to claim 3, wherein the GP2 isoforms are immobilized on a solid phase.

6. The method according to claim 3, wherein the kit comprises additionally
   one or more human anti-immunoglobulin antibodies, wherein said human anti-immunoglobulin antibodies bind autoantibodies of Ig-subtypes IgG and/or IgA, and
   a detectable label, capable of binding said human anti-Immunoglobulin antibody or linked to said human anti-Immunoglobulin antibody.

7. An in vitro method for detecting autoantibodies in a sample that bind to one or more isoforms of Glycoprotein 2 (GP2), comprising:
   providing the sample of a subject,
   providing two or more isoforms of GP2 comprising at least isoform 1 and/or 2 of GP2 and isoform 3 and/or 4 of GP2,
   contacting said sample with said isoforms of GP2,
   detecting IgG and/or the IgA autoantibodies that bind said isoform 1 and/or 2 of GP2 and isoform 3 and/or 4 of GP2 in the sample.

* * * * *

SEQUENCE LISTING

```
<160> NUMBER OF SEQ ID NOS: 8

<210> SEQ ID NO 1
<211> LENGTH: 537
<212> TYPE: PRT
<213> ORGANISM: Homo sapiens
```

```
<400> SEQUENCE: 1

Met Pro His Leu Met Glu Arg Met Val Gly Ser Gly Leu Leu Trp Leu
1               5                   10                  15

Ala Leu Val Ser Cys Ile Leu Thr Gln Ala Ser Ala Val Gln Arg Gly
            20                  25                  30

Tyr Gly Asn Pro Ile Glu Ala Ser Tyr Gly Leu Asp Leu Asp Cys
        35                  40                  45

Gly Ala Pro Gly Thr Pro Glu Ala His Val Cys Phe Asp Pro Cys Gln
50                  55                  60

Asn Tyr Thr Leu Leu Asp Glu Pro Phe Arg Ser Thr Glu Asn Ser Ala
65                  70                  75                  80

Gly Ser Gln Gly Cys Asp Lys Asn Met Ser Gly Trp Tyr Arg Phe Val
            85                  90                  95

Gly Glu Gly Gly Val Arg Met Ser Glu Thr Cys Val Gln Val His Arg
            100                 105                 110

Cys Gln Thr Asp Ala Pro Met Trp Leu Asn Gly Thr His Pro Ala Leu
            115                 120                 125

Gly Asp Gly Ile Thr Asn His Thr Ala Cys Ala His Trp Ser Gly Asn
130                 135                 140

Cys Cys Phe Trp Lys Thr Glu Val Leu Val Lys Ala Cys Pro Gly Gly
145                 150                 155                 160

Tyr His Val Tyr Arg Leu Glu Gly Thr Pro Trp Cys Asn Leu Arg Tyr
                165                 170                 175

Cys Thr Val Pro Arg Asp Pro Ser Thr Val Glu Asp Lys Cys Glu Lys
            180                 185                 190

Ala Cys Arg Pro Glu Glu Cys Leu Ala Leu Asn Ser Thr Trp Gly
            195                 200                 205

Cys Phe Cys Arg Gln Asp Leu Asn Ser Ser Asp Val His Ser Leu Gln
210                 215                 220

Pro Gln Leu Asp Cys Gly Pro Arg Glu Ile Lys Val Lys Val Asp Lys
225                 230                 235                 240

Cys Leu Leu Gly Gly Leu Gly Leu Gly Glu Glu Val Ile Ala Tyr Leu
            245                 250                 255

Arg Asp Pro Asn Cys Ser Ser Ile Leu Gln Thr Glu Glu Arg Asn Trp
            260                 265                 270

Val Ser Val Thr Ser Pro Val Gln Ala Ser Ala Cys Arg Asn Ile Leu
            275                 280                 285

Glu Arg Asn Gln Thr His Ala Ile Tyr Lys Asn Thr Leu Ser Leu Val
            290                 295                 300

Asn Asp Phe Ile Ile Arg Asp Thr Ile Leu Asn Ile Asn Phe Gln Cys
305                 310                 315                 320

Ala Tyr Pro Leu Asp Met Lys Val Ser Leu Gln Ala Ala Leu Gln Pro
            325                 330                 335

Ile Val Ser Ser Leu Asn Val Ser Val Asp Gly Asn Gly Glu Phe Ile
            340                 345                 350

Val Arg Met Ala Leu Phe Gln Asp Gln Asn Tyr Thr Asn Pro Tyr Glu
            355                 360                 365

Gly Asp Ala Val Glu Leu Ser Val Glu Ser Val Leu Tyr Val Gly Ala
370                 375                 380

Ile Leu Glu Gln Gly Asp Thr Ser Arg Phe Asn Leu Val Leu Arg Asn
385                 390                 395                 400

Cys Tyr Ala Thr Pro Thr Glu Asp Lys Ala Asp Leu Val Lys Tyr Phe
            405                 410                 415
```

-continued

```
Ile Ile Arg Asn Ser Cys Ser Asn Gln Arg Asp Ser Thr Ile His Val
            420                 425                 430

Glu Glu Asn Gly Gln Ser Ser Glu Ser Arg Phe Ser Val Gln Met Phe
            435                 440                 445

Met Phe Ala Gly His Tyr Asp Leu Val Phe Leu His Cys Glu Ile His
            450                 455                 460

Leu Cys Asp Ser Leu Asn Glu Gln Cys Gln Pro Ser Cys Ser Arg Ser
465                 470                 475                 480

Gln Val Arg Ser Glu Val Pro Ala Ile Asp Leu Ala Arg Val Leu Asp
                485                 490                 495

Leu Gly Pro Ile Thr Arg Arg Gly Ala Gln Ser Pro Gly Val Met Asn
            500                 505                 510

Gly Thr Pro Ser Thr Ala Gly Phe Leu Val Ala Trp Pro Met Val Leu
            515                 520                 525

Leu Thr Val Leu Leu Ala Trp Leu Phe
            530                 535

<210> SEQ ID NO 2
<211> LENGTH: 534
<212> TYPE: PRT
<213> ORGANISM: Homo sapiens

<400> SEQUENCE: 2

Met Pro His Leu Met Glu Arg Met Val Gly Ser Gly Leu Leu Trp Leu
1               5                   10                  15

Ala Leu Val Ser Cys Ile Leu Thr Gln Ala Ser Ala Val Gln Arg Gly
            20                  25                  30

Tyr Gly Asn Pro Ile Glu Ala Ser Ser Tyr Gly Leu Asp Leu Asp Cys
            35                  40                  45

Gly Ala Pro Gly Thr Pro Glu Ala His Val Cys Phe Asp Pro Cys Gln
        50                  55                  60

Asn Tyr Thr Leu Leu Asp Glu Pro Phe Arg Ser Thr Glu Asn Ser Ala
65                  70                  75                  80

Gly Ser Gln Gly Cys Asp Lys Asn Met Ser Gly Trp Tyr Arg Phe Val
            85                  90                  95

Gly Glu Gly Gly Val Arg Met Ser Glu Thr Cys Val Gln Val His Arg
            100                 105                 110

Cys Gln Thr Asp Ala Pro Met Trp Leu Asn Gly Thr His Pro Ala Leu
            115                 120                 125

Gly Asp Gly Ile Thr Asn His Thr Ala Cys Ala His Trp Ser Gly Asn
        130                 135                 140

Cys Cys Phe Trp Lys Thr Glu Val Leu Val Lys Ala Cys Pro Gly Gly
145                 150                 155                 160

Tyr His Val Tyr Arg Leu Glu Gly Thr Pro Trp Cys Asn Leu Arg Tyr
            165                 170                 175

Cys Thr Asp Pro Ser Thr Val Glu Asp Lys Cys Glu Lys Ala Cys Arg
            180                 185                 190

Pro Glu Glu Glu Cys Leu Ala Leu Asn Ser Thr Trp Gly Cys Phe Cys
            195                 200                 205

Arg Gln Asp Leu Asn Ser Ser Asp Val His Ser Gln Pro Gln Leu
        210                 215                 220

Asp Cys Gly Pro Arg Glu Ile Lys Val Lys Val Asp Lys Cys Leu Leu
225                 230                 235                 240

Gly Gly Leu Gly Leu Gly Glu Glu Val Ile Ala Tyr Leu Arg Asp Pro
```

245                 250                 255
Asn Cys Ser Ser Ile Leu Gln Thr Glu Glu Arg Asn Trp Val Ser Val
                260                 265                 270

Thr Ser Pro Val Gln Ala Ser Ala Cys Arg Asn Ile Leu Glu Arg Asn
            275                 280                 285

Gln Thr His Ala Ile Tyr Lys Asn Thr Leu Ser Leu Val Asn Asp Phe
        290                 295                 300

Ile Ile Arg Asp Thr Ile Leu Asn Ile Asn Phe Gln Cys Ala Tyr Pro
305                 310                 315                 320

Leu Asp Met Lys Val Ser Leu Gln Ala Ala Leu Gln Pro Ile Val Ser
                325                 330                 335

Ser Leu Asn Val Ser Val Asp Gly Asn Gly Glu Phe Ile Val Arg Met
                340                 345                 350

Ala Leu Phe Gln Asp Gln Asn Tyr Thr Asn Pro Tyr Glu Gly Asp Ala
            355                 360                 365

Val Glu Leu Ser Val Glu Ser Val Leu Tyr Val Gly Ala Ile Leu Glu
        370                 375                 380

Gln Gly Asp Thr Ser Arg Phe Asn Leu Val Leu Arg Asn Cys Tyr Ala
385                 390                 395                 400

Thr Pro Thr Glu Asp Lys Ala Asp Leu Val Lys Tyr Phe Ile Ile Arg
                405                 410                 415

Asn Ser Cys Ser Asn Gln Arg Asp Ser Thr Ile His Val Glu Glu Asn
                420                 425                 430

Gly Gln Ser Ser Glu Ser Arg Phe Ser Val Gln Met Phe Met Phe Ala
            435                 440                 445

Gly His Tyr Asp Leu Val Phe Leu His Cys Glu Ile His Leu Cys Asp
        450                 455                 460

Ser Leu Asn Glu Gln Cys Gln Pro Ser Cys Ser Arg Ser Gln Val Arg
465                 470                 475                 480

Ser Glu Val Pro Ala Ile Asp Leu Ala Arg Val Leu Asp Leu Gly Pro
                485                 490                 495

Ile Thr Arg Arg Gly Ala Gln Ser Pro Gly Val Met Asn Gly Thr Pro
            500                 505                 510

Ser Thr Ala Gly Phe Leu Val Ala Trp Pro Met Val Leu Leu Thr Val
        515                 520                 525

Leu Leu Ala Trp Leu Phe
    530

<210> SEQ ID NO 3
<211> LENGTH: 390
<212> TYPE: PRT
<213> ORGANISM: Homo sapiens

<400> SEQUENCE: 3

Met Pro His Leu Met Glu Arg Met Val Gly Ser Gly Leu Leu Trp Leu
1               5                   10                  15

Ala Leu Val Ser Cys Ile Leu Thr Gln Ala Ser Ala Val Gln Arg Val
                20                  25                  30

Pro Arg Asp Pro Ser Thr Val Glu Asp Lys Cys Glu Lys Ala Cys Arg
            35                  40                  45

Pro Glu Glu Glu Cys Leu Ala Leu Asn Ser Thr Trp Gly Cys Phe Cys
        50                  55                  60

Arg Gln Asp Leu Asn Ser Ser Asp Val His Ser Leu Gln Pro Gln Leu
65                  70                  75                  80

```
Asp Cys Gly Pro Arg Glu Ile Lys Val Lys Val Asp Lys Cys Leu Leu
                85                  90                  95
Gly Gly Leu Gly Leu Gly Glu Val Ile Ala Tyr Leu Arg Asp Pro
            100                 105                 110
Asn Cys Ser Ser Ile Leu Gln Thr Glu Glu Arg Asn Trp Val Ser Val
            115                 120                 125
Thr Ser Pro Val Gln Ala Ser Ala Cys Arg Asn Ile Leu Glu Arg Asn
    130                 135                 140
Gln Thr His Ala Ile Tyr Lys Asn Thr Leu Ser Leu Val Asn Asp Phe
145                 150                 155                 160
Ile Ile Arg Asp Thr Ile Leu Asn Ile Asn Phe Gln Cys Ala Tyr Pro
                165                 170                 175
Leu Asp Met Lys Val Ser Leu Gln Ala Ala Leu Gln Pro Ile Val Ser
            180                 185                 190
Ser Leu Asn Val Ser Val Asp Gly Asn Gly Glu Phe Ile Val Arg Met
            195                 200                 205
Ala Leu Phe Gln Asp Gln Asn Tyr Thr Asn Pro Tyr Glu Gly Asp Ala
    210                 215                 220
Val Glu Leu Ser Val Glu Ser Val Leu Tyr Val Gly Ala Ile Leu Glu
225                 230                 235                 240
Gln Gly Asp Thr Ser Arg Phe Asn Leu Val Leu Arg Asn Cys Tyr Ala
                245                 250                 255
Thr Pro Thr Glu Asp Lys Ala Asp Leu Val Lys Tyr Phe Ile Ile Arg
            260                 265                 270
Asn Ser Cys Ser Asn Gln Arg Asp Ser Thr Ile His Val Glu Glu Asn
            275                 280                 285
Gly Gln Ser Ser Glu Ser Arg Phe Ser Val Gln Met Phe Met Phe Ala
    290                 295                 300
Gly His Tyr Asp Leu Val Phe Leu His Cys Glu Ile His Leu Cys Asp
305                 310                 315                 320
Ser Leu Asn Glu Gln Cys Gln Pro Ser Cys Ser Arg Ser Gln Val Arg
                325                 330                 335
Ser Glu Val Pro Ala Ile Asp Leu Ala Arg Val Leu Asp Leu Gly Pro
            340                 345                 350
Ile Thr Arg Arg Gly Ala Gln Ser Pro Gly Val Met Asn Gly Thr Pro
            355                 360                 365
Ser Thr Ala Gly Phe Leu Val Ala Trp Pro Met Val Leu Leu Thr Val
    370                 375                 380
Leu Leu Ala Trp Leu Phe
385                 390

<210> SEQ ID NO 4
<211> LENGTH: 387
<212> TYPE: PRT
<213> ORGANISM: Homo sapiens

<400> SEQUENCE: 4

Met Pro His Leu Met Glu Arg Met Val Gly Ser Gly Leu Leu Trp Leu
1               5                   10                  15
Ala Leu Val Ser Cys Ile Leu Thr Gln Ala Ser Ala Val Gln Arg Asp
                20                  25                  30
Pro Ser Thr Val Glu Asp Lys Cys Glu Lys Ala Cys Arg Pro Glu Glu
            35                  40                  45
Glu Cys Leu Ala Leu Asn Ser Thr Trp Gly Cys Phe Cys Arg Gln Asp
    50                  55                  60
```

| Leu | Asn | Ser | Ser | Asp | Val | His | Ser | Leu | Gln | Pro | Gln | Leu | Asp | Cys | Gly |
| 65 | | | | 70 | | | | 75 | | | | 80 | | | |

Pro Arg Glu Ile Lys Val Lys Val Asp Lys Cys Leu Leu Gly Gly Leu
                85                  90                  95

Gly Leu Gly Glu Glu Val Ile Ala Tyr Leu Arg Asp Pro Asn Cys Ser
            100                 105                 110

Ser Ile Leu Gln Thr Glu Glu Arg Asn Trp Val Ser Val Thr Ser Pro
            115                 120                 125

Val Gln Ala Ser Ala Cys Arg Asn Ile Leu Glu Arg Asn Gln Thr His
 130                   135                 140

Ala Ile Tyr Lys Asn Thr Leu Ser Leu Val Asn Asp Phe Ile Ile Arg
145                   150                 155                 160

Asp Thr Ile Leu Asn Ile Asn Phe Gln Cys Ala Tyr Pro Leu Asp Met
            165                 170                 175

Lys Val Ser Leu Gln Ala Ala Leu Gln Pro Ile Val Ser Ser Leu Asn
            180                 185                 190

Val Ser Val Asp Gly Asn Gly Glu Phe Ile Val Arg Met Ala Leu Phe
            195                 200                 205

Gln Asp Gln Asn Tyr Thr Asn Pro Tyr Glu Gly Asp Ala Val Glu Leu
 210                   215                 220

Ser Val Glu Ser Val Leu Tyr Val Gly Ala Ile Leu Glu Gln Gly Asp
225                   230                 235                 240

Thr Ser Arg Phe Asn Leu Val Leu Arg Asn Cys Tyr Ala Thr Pro Thr
            245                 250                 255

Glu Asp Lys Ala Asp Leu Val Lys Tyr Phe Ile Ile Arg Asn Ser Cys
            260                 265                 270

Ser Asn Gln Arg Asp Ser Thr Ile His Val Glu Glu Asn Gly Gln Ser
            275                 280                 285

Ser Glu Ser Arg Phe Ser Val Gln Met Phe Met Phe Ala Gly His Tyr
            290                 295                 300

Asp Leu Val Phe Leu His Cys Glu Ile His Leu Cys Asp Ser Leu Asn
305                   310                 315                 320

Glu Gln Cys Gln Pro Ser Cys Ser Arg Ser Gly Val Arg Ser Glu Val
            325                 330                 335

Pro Ala Ile Asp Leu Ala Arg Val Leu Asp Leu Gly Pro Ile Thr Arg
            340                 345                 350

Arg Gly Ala Gln Ser Pro Gly Val Met Asn Gly Thr Pro Ser Thr Ala
            355                 360                 365

Gly Phe Leu Val Ala Trp Pro Met Val Leu Leu Thr Val Leu Leu Ala
 370                   375                 380

Trp Leu Phe
385

<210> SEQ ID NO 5
<211> LENGTH: 1614
<212> TYPE: DNA
<213> ORGANISM: Homo sapiens

<400> SEQUENCE: 5

| atgcctcacc | ttatggaaag | gatggtgggc | tctggcctcc | tgtggctggc | cttggtctcc | 60 |
| tgcattctga | cccaggcatc | tgcagtgcag | cgaggttatg | aaacccat | tgaagccagt | 120 |
| tcgtatgggc | tggacctgga | ctgcggagct | cctggcaccc | cagaggctca | tgtctgtttt | 180 |
| gaccctgtc | agaattacac | cctcctggat | gaacccttcc | gaagcacaga | gaactcagca | 240 |

```
gggtcccagg ggtgcgataa aaacatgagc ggctggtacc gctttgtagg ggaaggagga       300
gtaaggatgt cggagacctg tgtccaggtg caccgatgcc agacagacgc tcccatgtgg       360
ctgaatggga cccaccctgc ccttggggat ggcatcacca accacactgc ctgtgcccat       420
tggagtggca actgctgttt ctggaaaaca gaggtgctgg tgaaggcctg cccaggcggg       480
taccatgtgt accggttgga aggcactccc tggtgtaatc tgagatactg cacagttcca       540
cgagacccat ccactgtgga ggacaagtgt gagaaggcct gccgccccga ggaggagtgc       600
cttgccctca acagcacctg gggctgtttc tgcagacagg acctcaatag ttctgatgtc       660
cacagtttgc agcctcagct agactgtggg cccagggaga tcaaggtgaa ggtggacaaa       720
tgtttgctgg gaggcctggg tttggggag gaggtcattg cctacctgcg agacccaaac       780
tgcagcagca tcttgcagac agaggagagg aactgggtat ctgtgaccag ccccgtccag       840
gctagtgcct gcaggaacat tctggagaga aatcaaaccc atgccatcta caaaaacacc       900
ctctccttgg tcaatgattt catcatcaga gacaccatcc tcaacatcaa cttccaatgt       960
gcctacccac tggacatgaa agtcagcctc caagctgcct gcagcccat tgtaagttcc      1020 ctgaacgtca gtgtggacgg gaatggagag ttcattgtca ggatggccct cttccaagac      1080
cagaactaca cgaatcctta cgaaggggat gcagttgaac tgtctgttga gtccgtgctg      1140
tatgtgggtg ccatcttgga acaagggac acctcccggt ttaacctggt gttgaggaac      1200
tgctatgcca cccccactga agacaaggct gaccttgtga agtatttcat catcagaaac      1260
agctgctcaa atcaacgtga ttccaccatc cacgtggagg agaatgggca gtcctcggaa      1320
agccggttct cagttcagat gttcatgttt gctggacatt atgacctagt tttcctgcat      1380
tgtgagattc atctctgtga ttctcttaat gaacagtgcc agccttcttg ctcaagaagt      1440
caagtccgca gtgaagtacc ggccatcgac ctagcccggg ttctagattt ggggcccatc      1500
actcggagag gtgcacagtc tcccggtgtc atgaatggaa cccctagcac tgcagggttc      1560
ctggtggcct ggcctatggt cctcctgact gtcctcctgg cttggctgtt ctga           1614
```

<210> SEQ ID NO 6
<211> LENGTH: 1605
<212> TYPE: DNA
<213> ORGANISM: Homo sapiens

<400> SEQUENCE: 6

```
atgcctcacc ttatggaaag gatggtgggc tctggcctcc tgtggctggc cttggtctcc        60
tgcattctga cccaggcatc tgcagtgcag cgaggttatg gaaacccat tgaagccagt       120 tcgtatgggc tggacctgga ctgcggagct cctggcaccc cagaggctca tgtctgtttt       180 gaccctgtc agaattacac cctcctggat gaacccttcc gaagcacaga gaactcagca       240
gggtcccagg ggtgcgataa aaacatgagc ggctggtacc gctttgtagg ggaaggagga       300
gtaaggatgt cggagacctg tgtccaggtg caccgatgcc agacagacgc tcccatgtgg       360
ctgaatggga cccaccctgc ccttggggat ggcatcacca accacactgc ctgtgcccat       420
tggagtggca actgctgttt ctggaaaaca gaggtgctgg tgaaggcctg cccaggcggg       480
taccatgtgt accggttgga aggcactccc tggtgtaatc tgagatactg cacagaccca       540
tccactgtgg aggacaagtg tgagaaggcc tgccgccccg aggaggagtg ccttgccctc       600
aacagcacct ggggctgttt ctgcagacag gacctcaata gttctgatgt ccacagtttg       660
cagcctcagc tagactgtgg gcccagggag atcaaggtga aggtggacaa atgtttgctg       720
```

| | |
|---|---:|
| ggaggcctgg gtttggggga ggaggtcatt gcctacctgc gagacccaaa ctgcagcagc | 780 |
| atcttgcaga cagaggagag gaactgggta tctgtgacca gccccgtcca ggctagtgcc | 840 |
| tgcaggaaca ttctggagag aaatcaaacc catgccatct acaaaaacac cctctccttg | 900 |
| gtcaatgatt tcatcatcag agacaccatc ctcaacatca acttccaatg tgcctaccca | 960 |
| ctggacatga aagtcagcct ccaagctgcc ttgcagccca ttgtaagttc cctgaacgtc | 1020 |
| agtgtggacg ggaatggaga gttcattgtc aggatggccc tcttccaaga ccagaactac | 1080 |
| acgaatcctt acgaagggga tgcagttgaa ctgtctgttg agtccgtgct gtatgtgggt | 1140 |
| gccatcttgg aacaagggga cacctcccgg tttaacctgg tgttgaggaa ctgctatgcc | 1200 |
| accccccactg aagacaaggc tgaccttgtg aagtatttca tcatcagaaa cagctgctca | 1260 |
| aatcaacgtg attccaccat ccacgtggag gagaatgggc agtcctcgga agccggttc | 1320 |
| tcagttcaga tgttcatgtt tgctggacat tatgacctag ttttcctgca ttgtgagatt | 1380 |
| catctctgtg attctcttaa tgaacagtgc cagccttctt gctcaagaag tcaagtccgc | 1440 |
| agtgaagtac cggccatcga cctagcccgg gttctagatt tggggcccat cactcggaga | 1500 |
| ggtgcacagt ctcccggtgt catgaatgga ccccctagca ctgcagggtt cctggtggcc | 1560 |
| tggcctatgg tcctcctgac tgtcctcctg gcttggctgt tctga | 1605 |

<210> SEQ ID NO 7
<211> LENGTH: 1173
<212> TYPE: DNA
<213> ORGANISM: Homo sapiens

<400> SEQUENCE: 7

| | |
|---|---:|
| atgcctcacc ttatggaaag gatggtgggc tctggcctcc tgtggctggc cttggtctcc | 60 |
| tgcattctga cccaggcatc tgcagtgcag cgagttccac gagacccatc cactgtggag | 120 |
| gacaagtgtg agaaggcctg ccgccccgag gaggagtgcc ttgccctcaa cagcacctgg | 180 |
| ggctgtttct gcagacagga cctcaatagt tctgatgtcc acagtttgca gcctcagcta | 240 |
| gactgtgggc ccagggagat caaggtgaag gtggacaaat gtttgctggg aggcctgggt | 300 |
| ttgggggagg aggtcattgc ctacctgcga gacccaaact gcagcagcat cttgcagaca | 360 |
| gaggagagga actgggtatc tgtgaccagc cccgtccagg ctagtgcctg caggaacatt | 420 |
| ctggagagaa atcaaaccca tgccatctac aaaaacaccc tctccttggt caatgatttc | 480 |
| atcatcagag accatcct caacatcaac ttccaatgtg cctacccact ggacatgaaa | 540 |
| gtcagcctcc aagctgcctt gcagcccatt gtaagttccc tgaacgtcag tgtggacggg | 600 |
| aatggagagt tcattgtcag gatggccctc ttccaagacc agaactacac gaatccttac | 660 |
| gaaggggatg cagttgaact gtctgttgag tccgtgctgt atgtgggtgc catcttggaa | 720 |
| caaggggaca cctcccggtt taacctggtg ttgaggaact gctatgccac ccccactgaa | 780 |
| gacaaggctg accttgtgaa gtatttcatc atcagaaaca gctgctcaaa tcaacgtgat | 840 |
| tccaccatcc acgtggagga gaatgggcag tcctcggaaa gccggttctc agttcagatg | 900 |
| ttcatgtttg ctggacatta tgacctagtt ttcctgcatt gtgagattca tctctgtgat | 960 |
| tctcttaatg aacagtgcca gccttcttgc tcaagaagtc aagtccgcag tgaagtaccg | 1020 |
| gccatcgacc tagcccgggt tctagatttg ggcccatca ctcggagagg tgcacagtct | 1080 |
| cccggtgtca tgaatggaac ccctagcact gcagggttcc tggtggcctg gcctatggtc | 1140 |
| ctcctgactg tcctcctggc ttggctgttc tga | 1173 |

```
<210> SEQ ID NO 8
<211> LENGTH: 1164
<212> TYPE: DNA
<213> ORGANISM: Homo sapiens

<400> SEQUENCE: 8
atgcctcacc ttatggaaag gatggtgggc tctggcctcc tgtggctggc cttggtctcc      60
tgcattctga cccaggcatc tgcagtgcag cgagacccat ccactgtgga ggacaagtgt     120
gagaaggcct gccgccccga ggaggagtgc cttgccctca acagcacctg gggctgtttc     180
tgcagacagg acctcaatag ttctgatgtc cacagtttgc agcctcagct agactgtggg     240
cccagggaga tcaaggtgaa ggtggacaaa tgtttgctgg gaggcctggg tttggggag      300 gaggtcattg cctacctgcg agacccaaac tgcagcagca tcttgcagac agaggagagg     360
aactgggtat ctgtgaccag ccccgtccag gctagtgcct gcaggaacat tctgagaga      420 aatcaaaccc atgccatcta caaaaacacc ctctccttgg tcaatgattt catcatcaga     480
gacaccatcc tcaacatcaa cttccaatgt gcctaccac tggacatgaa agtcagcctc      540
caagctgcct tgcagcccat tgtaagttcc ctgaacgtca gtgtggacgg aatggagag      600 ttcattgtca ggatggccct cttccaagac cagaactaca cgaatcctta cgaaggggat     660
gcagttgaac tgtctgttga gtccgtgctg tatgtgggtg ccatcttgga caaggggac      720 acctcccggt ttaacctggt gttgaggaac tgctatgcca cccccactga agacaaggct     780
gaccttgtga agtatttcat catcagaaac agctgctcaa atcaacgtga ttccaccatc     840
cacgtggagg agaatgggca gtcctcggaa agccggttct cagttcagat gttcatgttt     900
gctggacatt atgacctagt tttcctgcat tgtgagattc atctctgtga ttctcttaat     960
gaacagtgcc agccttcttg ctcaagaagt caagtccgca gtgaagtacc ggccatcgac    1020
ctagcccggg ttctagattt ggggcccatc actcggagag gtgcacagtc tcccggtgtc    1080
atgaatggaa cccctagcac tgcagggttc ctggtggcct ggcctatggt cctcctgact    1140
gtcctcctgg cttggctgtt ctga                                            1164
```